United States Patent
Lopez et al.

(10) Patent No.: US 9,328,093 B2
(45) Date of Patent: May 3, 2016

(54) SELECTIVE INHIBITORS OF UBIQUITIN SPECIFIC PROTEASE 7, THE PHARMACEUTICAL COMPOSITIONS THEREOF AND THEIR THERAPEUTIC APPLICATIONS

(71) Applicant: HYBRIGENICS SA, Paris (FR)

(72) Inventors: Roman Lopez, Issy-les-Moulineaux (FR); Frederic Colland, Issy-les-Moulineaux (FR)

(73) Assignee: HYBRIGENICS SA, Paris (FR)

(*) Notice: Subject to any disclaimer, the term of this patent is extended or adjusted under 35 U.S.C. 154(b) by 0 days.

(21) Appl. No.: 14/488,601

(22) Filed: Sep. 17, 2014

(65) Prior Publication Data

US 2015/0072973 A1    Mar. 12, 2015

Related U.S. Application Data

(60) Division of application No. 13/521,978, filed as application No. PCT/EP2011/050523 on Jan. 17, 2011, now abandoned, which is a continuation of application No. 12/885,983, filed on Sep. 20, 2010, now abandoned.

(60) Provisional application No. 61/295,399, filed on Jan. 15, 2010.

(30) Foreign Application Priority Data

Aug. 13, 2010 (EP) .................................... 10172844

(51) Int. Cl.
| | |
|---|---|
| A61K 31/44 | (2006.01) |
| C07D 401/12 | (2006.01) |
| C07D 219/04 | (2006.01) |
| C07D 219/06 | (2006.01) |
| C07D 401/14 | (2006.01) |
| A61K 31/435 | (2006.01) |
| A61K 31/496 | (2006.01) |
| A61K 31/55 | (2006.01) |
| A61K 45/06 | (2006.01) |

(52) U.S. Cl.
CPC ............ *C07D 401/12* (2013.01); *A61K 31/435* (2013.01); *A61K 31/496* (2013.01); *A61K 31/55* (2013.01); *A61K 45/06* (2013.01); *C07D 219/04* (2013.01); *C07D 219/06* (2013.01); *C07D 401/14* (2013.01)

(58) Field of Classification Search
CPC ...................................................... C07D 219/04
USPC .......................................................... 514/297
See application file for complete search history.

(56) References Cited

U.S. PATENT DOCUMENTS

| | | | | |
|---|---|---|---|---|
| 1,886,481 | A | * 11/1932 | Hartmann et al. | ............... 546/90 |
| 2009/0163545 | A1 | * 6/2009 | Goldfarb | ........................ 514/312 |

FOREIGN PATENT DOCUMENTS

EP           1 749 822 A1    2/2007

OTHER PUBLICATIONS

Bapat, Journal of Pharmacology and Experimental Therapeutics (2010), 334(3), 988-998.*
Devlin, High Throughput Screening: The Discovery of Bioactive Substance, Edited by John P. Devlin, Marcel Dekker Inc. 1997.*
Dorwald F. A. Side Reactions in Organic Synthesis, 2005, Wiley: VCH, Weinheim p. IX of Preface p. 1-15.
Venkatesh et al., J. Pharm. Sci. 89, 145-54 (2000).
IDS NPL document filed Nov. 11, 2013.
Chinese Search Report issued in corresponding CN Application No. 201180010555.9, dated Aug. 15, 2013.
RN904444-73-1 Registry, STN International, Copyright © 2013 American Chemical Society (ACS), pp. 1-3, STN International Session, Aug. 25, 2006.
RN904449-06-5 Registry, STN International, Copyright © 2013 American Chemical Society (ACS), pp. 1-3, STN International Session, Aug. 25, 2006.
RN904448-58-4 Registry, STN International, Copyright © 2013 American, Chemical Society (ACS), pp. 1-13, STN International Session, Aug. 25, 2006.
Bapat, A., et al. "Novel Small-Molecule Inhibitor of Apurinic/Apyrimidinic Endonuclease 1 Blocks Proliferation and Reduces Viability of Glioblastoma Cells," Journal of Pharmacology and Experimental Therapeutics, Sep. 2010; pp. 988-998.
Abstract of Hughes. G.K, et al., "Derivatives of 4-Hydroxyquinoline", J. & Proc. Royal Soc. New South Wales, vol. 71.
European Search Report and Written Opinion issued in corresponding EP Application No. PCT/EP2011/050523, dated Feb. 15, 2011.

\* cited by examiner

*Primary Examiner* — Nizal Chandrakumar
(74) *Attorney, Agent, or Firm* — Davidson, Davidson & Kappel LLC

(57) ABSTRACT

The present invention concerns the discovery of new selective inhibitors of ubiquitin specific proteases, their process of preparation and their therapeutic use.

4 Claims, 5 Drawing Sheets

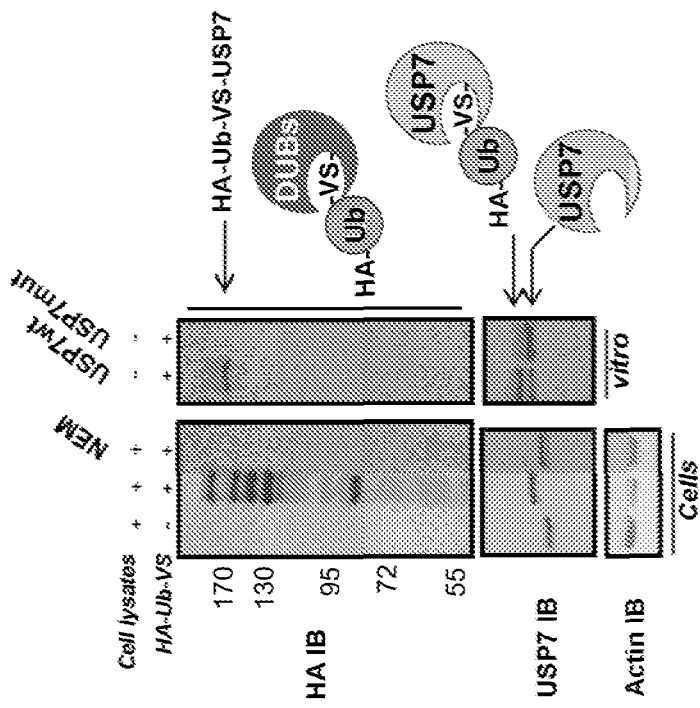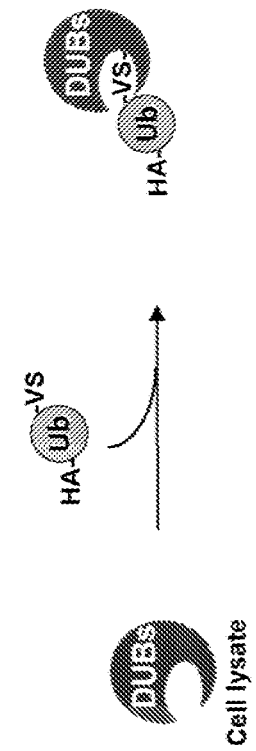
Fig. 1A
Fig. 1B

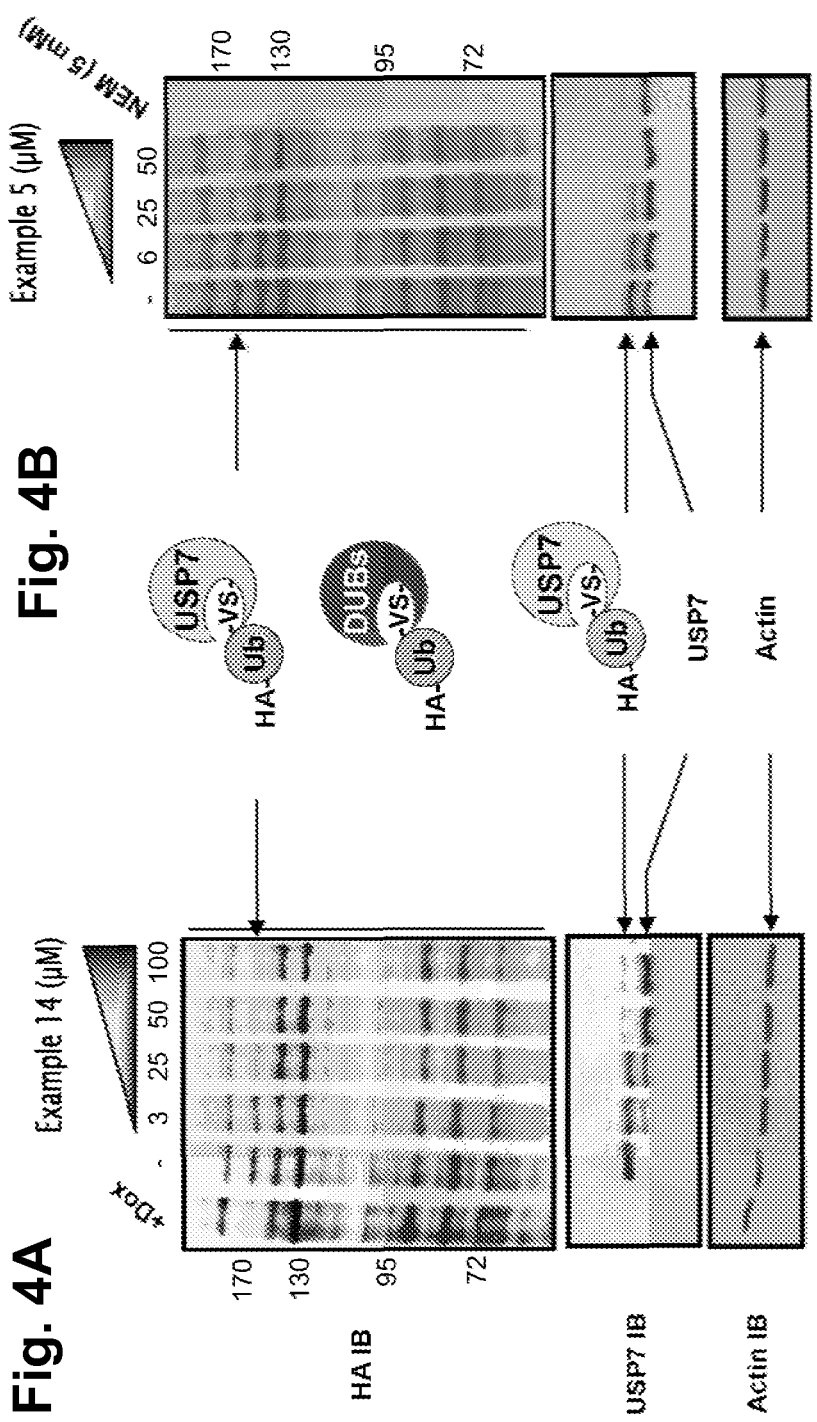

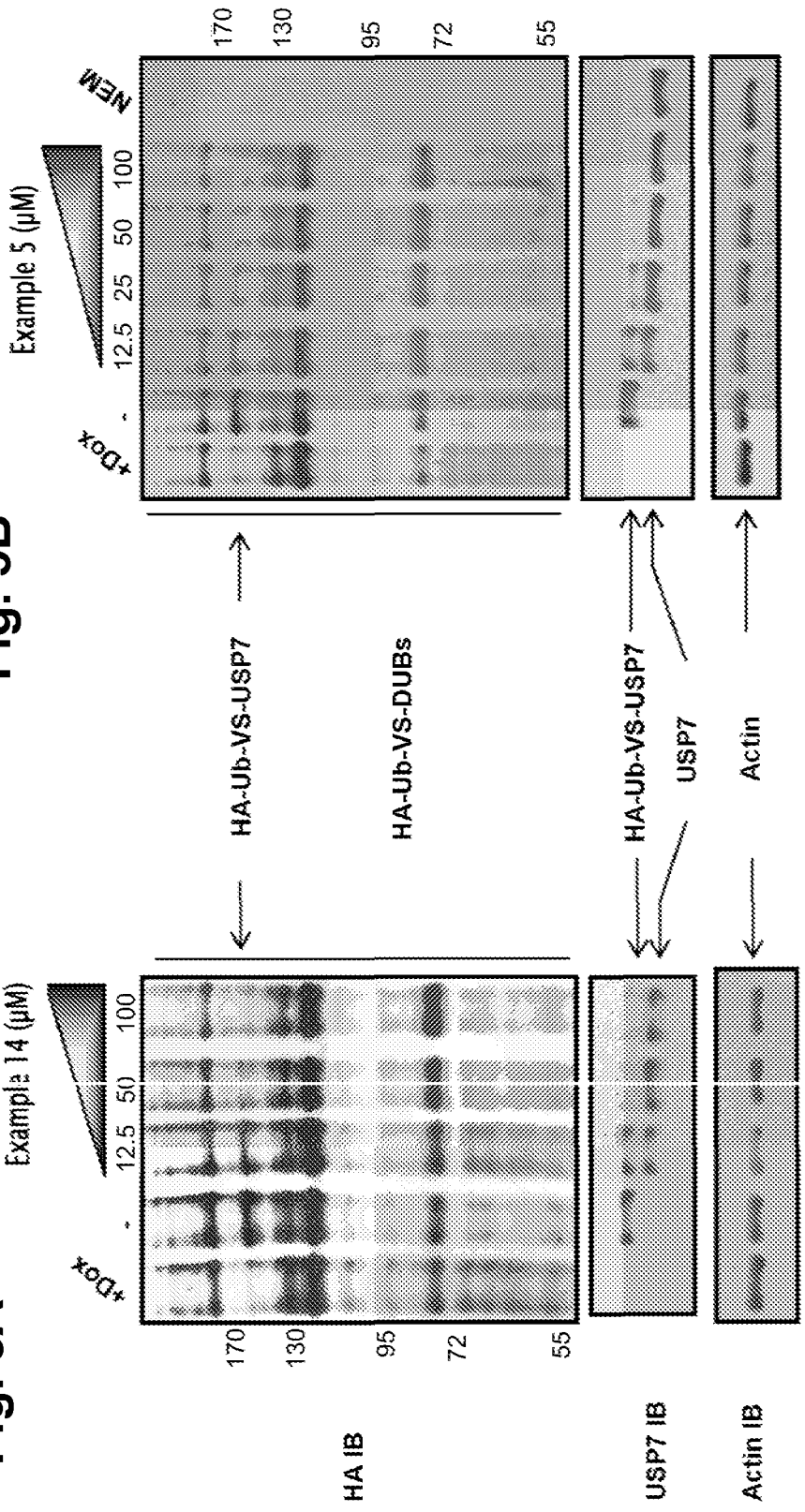

SELECTIVE INHIBITORS OF UBIQUITIN SPECIFIC PROTEASE 7, THE PHARMACEUTICAL COMPOSITIONS THEREOF AND THEIR THERAPEUTIC APPLICATIONS

This application is a divisional of U.S. patent application Ser. No. 13/521,978, filed on Jul. 12, 2012, which is a national phase application under 35 U.S.C. §371 of International Application No. PCT/EP2011/050523, filed on Jan. 17, 2011, which claims priority to EP 10172844.2, filed on Aug. 13, 2010, and U.S. application Ser. No. 12/885,983, filed on Aug. 13, 2010, which claims priority to U.S. Application No. 61/295,399, filed on Jan. 15, 2010, the disclosures of which are all hereby incorporated by reference herein.

FIELD OF THE INVENTION

The present invention concerns the discovery of new selective inhibitors of ubiquitin specific proteases, their process of preparation and their therapeutic use.

BACKGROUND OF THE INVENTION

Ubiquitin specific proteases (USP) are cysteines proteases which belong to the deubiquitinylation enzymes (DUBs) family.

Deregulation of the ubiquitin-proteasome system has been implicated in the pathogenesis of many human diseases, including cancer (Hoeller et al. *Nat Rev Cancer* 2006, 6(10), 776-788), neurodegenerative disorders (Rubinsztein, *Nature* 2006, 443(7113), 780-786) and viral diseases (Gao & Luo *Can J Physiol Pharmacol* 2006, 84(1), 5-14). The market success of the proteasome inhibitor Velcade® (bortezomib) for the treatment of multiple myeloma and mantle cell lymphoma has established this system as a valid target for cancer treatment (Adams, *Nat Rev Cancer* 2004, 4(5), 349-360). A promising alternative to targeting the proteasome itself would be to interfere with the upstream ubiquitin conjugation/deconjugation machinery, to generate more specific, less toxic anticancer agents.

Mono- and polyubiquitination can be reversed by deubiquitinating enzymes, which specifically cleave the isopeptide bond at the C-terminus of ubiquitin. Ubiquitin specific proteases and ubiquitin C-terminal hydrolases (UCH) enzymes are the best characterized members of the DUB family (Komander et al. *Nat. Rev. Mol. Cell Biol.* 2009, 10(8), 550-63; Nijman et al. *Cell* 2005, 123(5), 773-786). UCHs are thought to cleave small protein substrates preferentially and to be involved principally in the processing and recycling of ubiquitin, but their specific functions remain poorly understood. USPs constitute the largest subfamily of DUBs, with more than 60 members. They remove ubiquitin from specific protein substrates, thus preventing their targeting to the proteasome or regulating their subcellular localization and activation (Daviet & Colland, *Biochimie* 2008, 90(2), 270-83). USPs are emerging as potential targets for pharmacological interference with the ubiquitin regulation machinery, based on their protease activity and involvement in several human diseases.

USP7 (Ubiquitin Specific Protease 7)/HAUSP (Herpes Associated Ubiquitin Specific Protease) is a 135 kDa protein of the USP family. USP7 has been shown to interact with viral proteins, such as ICP0 (Vmw 110), a herpes simplex virus immediate-early gene stimulating initiation of the viral lytic cycle (Everett et al., *J Virol* 73, 1999, 417-426), and EBNA1 (Epstein-Barr Nuclear Antigen-1) (Holowaty et al., *J Biol Chem* 2003, 278, 29987-29994 and 47753-47761). Human proteins, such as p53 and the major E3 ligase of p53, Mdm2, have also been identified as partners and substrates of USP7 (Cummins et al. *Nature* 2004, 486, Cummins & Vogelstein, *Cell Cycle,* 2004, 3, 689-692; Li et al. *Mol Cell* 2004, 13, 879-886; Li et al. *Nature* 2002, 416, 648-653). More generally USP7 can deubiquitinate different targets, including Mdm2 and p53, and the net deubiquitination of these latter targets ultimately determines functional p53 levels. Consistent with recent reports, USP7 silencing has also been shown to increase steady-state p53 levels by promoting Mdm2 degradation. Binding of USP7 to p53 was recently shown to be regulated by TSPYL5, a protein potentially involved in breast oncogenesis through a competition with p53 for binding to the same region of USP7 (Epping et al., *Nat Cell Biol.* 2011, 13(1):102-8). More recently, both upregulation and downregulation of USP7 have been shown to inhibit colon cancer cell proliferation in vitro and tumor growth in vivo, by resulting in constitutively high p53 levels (Becker et al. *Cell Cycle* 2008, 7(9), 1205-13).

USP7 also alters the level of the P16$^{INK4a}$ tumor suppressor through Bmi1/Me118 stabilization (Maertens et al., *Embo J.* 2010 29, 2553-2565). Additional proteins involved in genomic integrity/regulation such as the DNMT1 DNA methylase and the Claspin adaptor are also stabilized by USP7 (Du et al., *Science Signaling* 2010, 3(146):ra80; Faustrup et al., *J. Cell Biol.* 2009, 184(1):13-9). Importantly, the abundance of USP7 and DNMT1, a protein involved in maintaining epigenetic methylation required to silence genes involved in development and cancer, correlates in human colon cancer (Du et al., *Science Signaling,* 2010, 3(146): ra80). USP7 has also been shown in human cells to deubiquitinate the well-known tumor suppressor gene PTEN, which provokes its nuclear export and hence its inactivation (Song et al., *Nature* 2008, 455(7214), 813-7). More importantly, USP7 overexpression was reported for the first time in prostate cancer and this overexpression was directly associated with tumour aggressiveness (Song et al., *Nature* 2008, 455(7214), 813-7).

USP7 has also been shown in human cells to deubiquitinate FOXO4, which provokes its nuclear export and hence its inactivation; consequently the oncogenic PI3K/PKB signaling pathway was activated (van der Horst et al., *Nat Cell Biol.* 2006, 8, 1064-1073) Finally, USP7 plays an important role in p53-mediated cellular responses to various types of stress, such as DNA damage and oxidative stress (Marchenko et al., *Embo J.* 2007 26, 923-934, Meulmeester et al. *Mol Cell* 2005, 18, 565-576, van der Horst et al., *Nat Cell Biol.* 2006, 8, 1064-1073).

Synthetic inhibitors of USP7 protein binding containing the polypeptide portion $P^1$-Gly-$P^3$-Ser, where $P^1$ is a glutamic acid residue or an amino acid with a non polar side chain and $P^3$ is a glycine residue or an amino acid with non polar side chain, have been reported (WO2006072048).

The phenotypes associated with USP7 silencing and the known connections between USP7 and essential viral proteins and oncogenic pathways, such as the p53/Mdm2 and PI3K/PKB pathways, strongly suggest that targeting USP7 with small-molecule inhibitors may be beneficial in the treatment of cancers and viral diseases. An inhibitor against USP7 was recently reported (Colland et al. *Molecular Cancer Therapeutics* 2009, 8, 2286-95 and EP 1 749 822).

However, to date, no specific USP7 small molecule inhibitors seem to have been reported.

SUMMARY OF THE INVENTION

According to a first object, the present invention concerns a compound of formula (I):

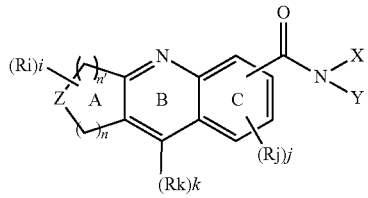

wherein:

i is an integer chosen from 0, 1, 2 or 3 when n is 1, or from 0, 1, 2, 3 or 4 when n is 2, or from 0, 1, 2, 3, 4 or 5 when n is 3;

j is an integer chosen from 0, 1, 2 or 3;

k is an integer chosen from 0 or 1;

n and n' identical or different are integers chosen from 0, 1, 2 or 4, provided that n+n' 4;

Z is $CH_2<$, —HC<, —N<, NH< or O<;

each Ri located on any available position of the A ring is identical or different and chosen from halogen, alkyl, aryl, -alkylaryl, OR, NRR', CN, $CF_3$, COR, COOR, CONRR';

each Rj located on any available position of the C ring is identical or different and chosen from halogen, alkyl, aryl, -alkylaryl, OR, NRR', CN, COR, COOR, CONRR';

Rk is independently chosen from halogen, alkyl, alkoxy, cyano;

X is chosen from H, alkyl, aryl, -alkylaryl, wherein said alkyl and/or aryl is optionally substituted by halogen, alkyl, CN, $CF_3$, OR, NRR', COR, COOR, CONRR';

Y is chosen from:

$(CT_2')_p$NRaRb where

Ra and Rb, identical or different, are independently chosen from H, alkyl, aryl or arylalkyl, wherein said aryl is optionally substituted by halogen, alkyl, CN, $CF_3$, =O, OR, NRR', COR, COOR, CONRR';

or Ra and Rb together form with the N atom to which they are attached a N comprising 5 to 7-membered heterocycle which may comprise one or two more heteroatoms chosen from N, O or S, said heterocycle being optionally substituted by one or more of halogen; =O; alkyl; -alkylaryl or aryl wherein said aryl is optionally substituted by halogen; CN; $CF_3$; OR; NRR'; COR; COOR; CONRR'; said heterocycle being optionally fused with an aryl;

p is an integer chosen from 0 to 6;

each T', identical or different is independently chosen from H or a linear or branched alkyl wherein the alkyl is optionally substituted by one or more OR, aryl; in one embodiment at least one of T' is different from H;

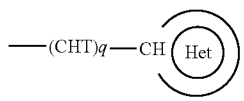

wherein:

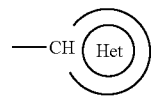

is a saturated or partially unsaturated heterocycle or heteroaryl, mono or bicyclic, comprising 1, 2 or 3 heteroatom(s) chosen from N, O or S, optionally substituted by one or more of alkyl; -alkylaryl; OR; C(=O)OR; =O; CN; $CF_3$; COR; NRR'; CONRR'; aryl or -alkylaryl wherein said aryl is optionally substituted by a linear or branched alkyl, halogen, OR, COR or NR'R;

q is an integer chosen from 0 to 6;

each T, identical or different is independently chosen from H or alkyl;

$(CHT)_r$-aryl wherein:

said mono or bicyclic aryl is optionally substituted by one or more of alkyl; OR; $CF_3$, $SO_2$NRR'; —C(=O)—R; Halogen; CN; —NRR'; CONRR; C(=O)—Oalkyl wherein said alkyl is optionally substituted by NRR' or NR"R'"; and/or said mono or bicyclic aryl is optionally fused with a monocyclic 5 to 7 membered heterocycle;

r is an integer chosen from 0 to 6;

each T, identical or different is independently chosen from H or alkyl; where R" and R'" together form with the N atom to which they are attached a N comprising 5 to 7-membered heterocycle which may comprise one or two more heteroatoms chosen from N, O or S, said heterocycle being optionally substituted by one or more of halogen; alkyl; CN; $CF_3$; OR; NRR'; COR; COOR; CONRR';

$(CHT)_s$-(C3-C7)cycloalkyl where s is an integer chosen from 0 to 6;

each T, identical or different is independently chosen from H or alkyl;

said cycloalkyl is monocyclic, or fused with an aryl; alkyl optionally substituted by CN, Oalkyl;

U—$S(O)_t$-alkyl where t is an integer chosen from 0, 1 or 2;

—U— is an alkylene optionally substituted by one or more of OR; =O; $CF_3$, $SO_2$NRR'; —C(=O)—R; Halogen; CN; —NRR'; CONRR; C(=O)OR;

or X and Y together form with the N atom to which they are attached an heterocycle comprising said N atom and optionally one or two more heteroatoms, said heterocyle being optionally insaturated and/or being optionally substituted by one or more of: =O; Hal, CN, NRR', C(=O)alkyl, alkyl; cycloalkyl; heterocycle; C(=O)—Oalkyl; -alkylheterocycle; aryl or -alkylaryl where said aryl is optionally fused with an heterocycle and/or said aryl being optionally substituted by alkyl or COalkyl; said heterocycle being optionally substituted by an alkyl;

being optionally fused with an aryl;

where R and R', identical or different are independently chosen from H, alkyl, aryl, -alkylaryl, or a tautomer thereof, and/or a pharmaceutically acceptable salt thereof.

The formula (I) of the invention refers to any of the following embodiment or any of their combinations.

According to a particular embodiment, formula (I) does not encompass those compounds where Hal is Cl, i=j=0, and n'=1, n=1, X is H or a C1-2alkyl and Y is a phenyl optionally substituted by one or two C1-C2alkyl, or n'=1, n=2, and:

X is H and Y is a phenyl substituted by CN or —C(=O)CH3; or

X and Y together form a piperazinyl ring substituted by a methoxyphenyl or fluorophenyl; or X and Y together form a piperidyl ring substituted by a piperidyl; or one of X is H and Y is a piperidyl substituted with COOEt.

In particular, compounds of the invention may be of the following formula:

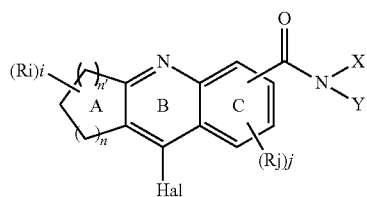

where Hal is chosen from F, Cl, Br or I.

Particular compounds are those of formula (I), wherein:

i=j=0; and/or

X is chosen from H, alkyl optionally substituted by CN;

Y is as defined above;

or X and Y together form with the N atom to which they are attached an heterocycle comprising said N atom and optionally one or two more heteroatoms, said heterocyle being optionally insaturated and/or being optionally substituted by one or more of: =O; Hal, CN, NRR', C(=O)alkyl, alkyl; cycloalkyl; heterocycle; C(=O)—Oalkyl; -alkylheterocycle; aryl or -alkylaryl where said aryl is optionally fused with an heterocycle and/or said aryl being optionally substituted by alkyl or COalkyl; said heterocycle being optionally substituted by an alkyl;

being optionally fused with an aryl.

In particular, the A ring is chosen from:

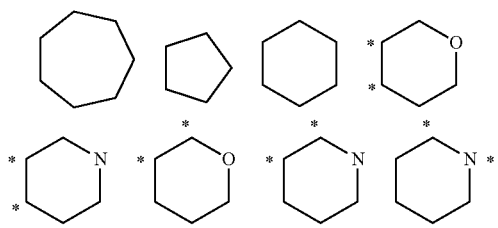

Preferably, n' is 0, 1 or 2 and n is 3, 2 or 1.

In particular, in formula (I), n' is 1 and n is 2.

More preferably A is

According to an embodiment, Hal is F, Br or I.

According to a further embodiment:

X is defined as above and Y is chosen from:

$(CT_2')_p$NRaRb where

Ra and Rb, identical or different, are independently chosen from H, alkyl, aryl, -alkylaryl, wherein said aryl is optionally substituted by alkyl;

p is 0 to 4.

or where

Ra and Rb together form with the N atom to which they are attached a 5 to 7-membered heterocycle optionally comprising one or two more heteroatoms chosen from N, O or S, said heterocycle being optionally substituted by one or more of halogen; =O; alkyl; -alkylaryl or aryl where aryl is optionally substituted by halogen; =O; CN; $CF_3$; OR; NRR'; COR; COOR; CONRR'; said heterocycle being optionally fused with an aryl and;

p is chosen from 2 or 3;

each T', identical or different, is independently chosen from H or a linear or branched alkyl, wherein the alkyl is optionally substituted by one or more OR, aryl; in one embodiment at least one of T' is different from H;

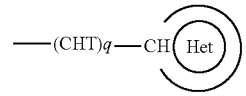

wherein:

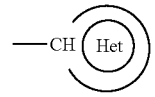

is a bicyclic saturated or partially unsaturated heterocycle or heteroaryl, comprising 1, 2 or 3 heteroatom(s) chosen from N, O or S, optionally substituted by one or more of alkyl; OR; C(=O)OR; aryl or -alkylaryl wherein said aryl is optionally substituted by alkyl, halogen, OR, COR or NR'R;

q is an integer chosen from 0, 1, 2 or 3;

each T, identical or different is independently chosen from H or alkyl;

$(CHT)_r$-aryl wherein:

said aryl is mono or bicyclic, optionally substituted by one or more of alkyl, OR, $SO_2$NRR'; —C(=O)—R; Halogen; CN; C(=O)—Oalkyl, wherein said alkyl is optionally substituted by NRR' or NR"R'"; and said aryl is optionally fused with an heterocycle;

r is an integer chosen from 0, 1, 2 or 3;

each T, identical or different is independently chosen from H or alkyl;

or

X and Y together form with the N atom to which they are attached an heterocycle comprising said N atom and optionally one or two more heteroatoms, said heterocycle being optionally insaturated and/or being optionally substituted by one or more of: =O; alkyl; cycloalkyl; heterocycle; -alkylheterocycle; C(=O)—Oalkyl; aryl or -alkylaryl where said aryl is optionally substituted by alkyl; said heterocycle being optionally substituted by an alkyl;
being optionally fused with an aryl;
where, preferably, q is 1, 2 or 3, r is 1, 2 or 3.
More particularly, in formula (I):
n'=1 and n=2 or 3;
X is defined as above and Y is chosen from:
$(CT_2')_p$NRaRb where
  Ra and Rb, identical or different, are independently chosen from H, alkyl, aryl, -alkylaryl, wherein said aryl is optionally substituted by halogen, alkyl, CN, $CF_3$, OR, NRR', COR, COOR, CONRR';
  or Ra and Rb together form with the N atom to which they are attached a N comprising 5 to 7-membered heterocycle optionally comprising one or two more heteroatoms chosen from N, O or S, said heterocycle being optionally substituted by one or more of halogen; alkyl; -alkylaryl or aryl wherein said aryl is optionally substituted by halogen; =O; CN; $CF_3$; OR; NRR'; COR; COOR; CONRR'; said heterocycle being optionally fused with an aryl;
  p is an integer chosen from 2 to 3;
  each T', identical or different is independently chosen from H or a linear or branched alkyl; wherein the alkyl is optionally substituted by one or more OR, aryl; in one embodiment at least one of T' is different from H;
  or

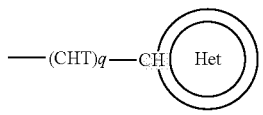

wherein:

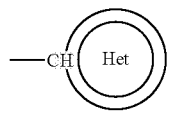

is saturated or partially unsaturated heterocycle or heteroaryl, mono or bicyclic, comprising 1, 2 or 3 heteroatom(s) chosen from N, O or S, optionally substituted by one or more of alkyl; -alkylaryl; OR; C(=O)OR; =O; CN; $CF_3$; COR; NRR'; CONRR'; aryl; wherein said aryl is optionally substituted by alkyl, halogen, OR, COR or NR'R;
q is 1, 2 or 3;
each T, identical or different is independently chosen from H or alkyl;
$(CHT)_r$-aryl wherein:
  said aryl is a monocyclic aryl and is optionally substituted by one or more of alkyl, $SO_2NRR'$; —C(=O)—R; CN; C(=O)—Oalkyl; wherein said alkyl is substituted by NRR' or NR"R'";
  r is an integer chosen from 0 to 6;
  each T, identical or different is independently chosen from H or alkyl; where R" and R'" together form with the N atom to which they are attached a N comprising 5 to 7-membered heterocycle which may comprise one or two more heteroatoms chosen from N, O or S, said heterocycle being optionally substituted by one or more of halogen; alkyl; CN; $CF_3$; OR; NRR'; COR; COOR; CONRR';

or X and Y together form with the N atom to which they are attached an heterocycle comprising said N atom and optionally one or two more heteroatoms, said heterocycle being optionally insaturated and/or
  being optionally substituted by one or more of: =O; alkyl; cycloalkyl; heterocycle; -alkylheterocycle; C(=O)—Oalkyl; -alkylaryl where said aryl is optionally fused with an heterocycle and/or said aryl being optionally substituted by alkyl or COalkyl; said heterocycle comprising one or two nitrogen atom and being optionally substituted by an alkyl;
  being optionally fused with an aryl;
where R and R', identical or different are independently chosen from H, alkyl, aryl, -alkylaryl.
More preferably in formula (I):
n'=1, n=2 or 3;
X is chosen from H, alkyl, aryl, -alkylaryl, wherein said alkyl and/or aryl is optionally substituted by halogen, alkyl, CN, $CF_3$, OR, NRR', COR, COOR, CONRR';
and Y is chosen from:
$(CT_2')_p$NRaRb where
  Ra and Rb, identical or different, are independently chosen from H, alkyl, aryl, -alkylaryl, wherein said aryl is optionally substituted by halogen, alkyl, CN, $CF_3$, OR, NRR', COR, COOR, CONRR';
  p is 1, 2 or 3; or
  Ra and Rb together form with the N atom to which they are attached a N comprising 5 to 7-membered heterocycle wherein the carbon atom adjacent to the heteroatom is optionally substituted by an alkyl; said heterocycle being optionally fused with an aryl;
  p is 3 or 4; or
  Ra and Rb together form with the N atom to which they are attached a N comprising 5 to 7-membered heterocycle which may comprise one or two more heteroatoms chosen from N, O or S, said heterocycle being optionally substituted by one or more of halogen; =O; alkyl; -alkylaryl or aryl wherein said aryl is optionally substituted by halogen; CN; $CF_3$; OR; NRR'; COR; COOR; CONRR';
  p is an integer chosen from 0 to 6;
  each T', identical or different, is independently chosen from H or a linear or branched alkyl, wherein the alkyl is optionally substituted by one or more OR, aryl, and at least one of T' is different from H.
$(CHT)_r$-aryl wherein:
  said aryl is a monocyclic aryl and is optionally substituted by one or more of alkyl, $SO_2NRR'$; —C(=O)—R; CN; C(=O)—Oalkyl; wherein said alkyl is substituted by NRR' or NR"R'";
  r is an integer chosen from 0 to 6;
  each T, identical or different is independently chosen from H or alkyl;

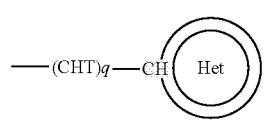

wherein:

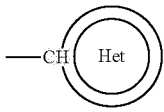

is a saturated monocyclic five membered heterocycle comprising a nitrogen atom and substituted by an alkyl, provided that the alkyl is not an ethyl, -alkylaryl, OR; C(=O)OR; =O; CN; CF₃; COR; NRR'; CONRR'; aryl; wherein said aryl is optionally substituted by alkyl, halogen, OR, COR or NR'R; or a monocyclic 6 membered heterocycle comprising an nitrogen atom and optionally substituted by one or more of -alkylaryl, OR; C(=O) OR; =O; CN; CF₃; COR; NRR'; CONRR'; aryl; wherein said aryl is optionally substituted by halogen, COR, OR or NR'R;

q is an integer chosen from 0 to 6;

each T, identical or different is independently chosen from H or alkyl.

or X and Y together form with the N atom to which they are attached an heterocycle comprising said N atom and optionally one or two more heteroatoms, said heterocyle being optionally insaturated and/or being optionally substituted by one or more of: =O; alkyl; cycloalkyl; heterocycle; -alkylheterocycle; C(=O)—Oalkyl; -alkylaryl where said aryl is optionally fused with an heterocycle and/or said aryl being optionally substituted by alkyl or COalkyl; said heterocycle comprising one or two nitrogen atom and being optionally substituted by an alkyl;

being optionally fused with an aryl;

In particular, compounds of the invention may be of the following formula

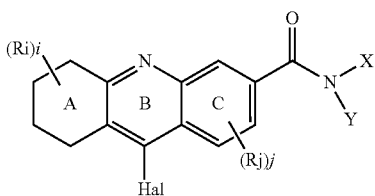

wherein:
i is an integer chosen from 0, 1, 2, 3 or 4; preferably i=0
j is an integer chosen from 0, 1, 2 or 3; preferably j=0
each Ri located on any available position of the A ring is identical or different and chosen from halogen, alkyl, aryl, -alkylaryl, OR, NRR', CN, CF₃, COR, COOR, CONRR';
each Rj located on any available position of the C ring is identical or different and chosen from halogen, alkyl, aryl, -alkylaryl, OR, NRR', CN, COR, COOR, CONRR';
X is H
Y is chosen from:
(CHT)$_r$-aryl wherein:
said aryl is a monocyclic aryl and is optionally substituted by one or more of alkyl, SO₂NRR'; —C(=O)—R; CN; —NRR', CONRR, C(=O)—Oalkyl; wherein said alkyl is substituted by NRR' or NR"R'"; preferably the aryl is a phenyl substituted by an alkyl substituted by NR"R'"

r is an integer chosen from 0 to 6; preferably r is 0 or 1;
each T is H;
where R" and R'" together form with the N atom to which they are attached a N comprising 5 to 7-membered heterocycle which may comprise one or two more heteroatoms chosen from N, O or S, said heterocycle being optionally substituted by one or more of halogen; alkyl; CN; CF₃; OR; NRR'; COR; COOR; CONRR'; preferably R" and R'" together form with the N atom to which they are attached a 5-membered heterocycle optionally substituted by one or more of halogen; alkyl; CN; CF₃; OR; NRR'; COR; COOR; CONRR'; preferably R" and R'" together form with the N atom to which they are attached a 5-membered heterocycle;
where R and R', identical or different are independently chosen from H, alkyl, aryl, -alkylaryl;
preferably the aryl is a phenyl substituted by an alkyl substituted by NR"R'" and R" and R'" together form with the N atom to which they are attached a 5-membered heterocycle;
(CT₂')$_p$NRaRb where
when each T' is H,
Ra and Rb together form with the N atom to which they are attached
a N comprising 6-membered mono substituted heterocycle wherein the carbon atom adjacent to the heteroatom is substituted by an alkyl; and p is 1, 3 or 4; preferably p is 4 or
a N-comprising 6-membered heterocycle and p is 1 to 4, preferably p is 1 to 3, for example p is 2; or
a N-comprising 5-membered heterocycle wherein the carbon atom adjacent to the heteroatom is substituted by an alkyl; and p is 1 to 4, preferably p is 1, 2 or 3; preferably p is 2 or 3; or
a N-comprising 7-membered heterocycle optionally substituted by an alkyl and p is 1, 2 or 4, preferably p is 2;
a N-comprising 5-membered heterocycle and p is 1, 2 or 4;
a N-comprising 5- to 7-membered heterocycle substituted by one or more of halogen, -alkylaryl, or aryl, wherein said aryl is optionally substituted by
one or more of halogen, —CN, CF₃; OR; NRR'; COR; COOR; CONRR';
where R and R', identical or different are independently chosen from H, alkyl, aryl, -alkylaryl;
Preferably: Ra and Rb together form with the N atom to which they are attached
a N comprising 6-membered mono substituted heterocycle wherein the carbon atom adjacent to the heteroatom is substituted by an alkyl; and p is 1, 3 or 4; preferably p is 4 or
a N-comprising 6-membered heterocycle and p is 1 to 4, preferably p is 1 to 3, for example p is 2; or
a N-comprising 5-membered heterocycle wherein the carbon atom adjacent to the heteroatom is substituted by an alkyl; and p is 1 to 4, preferably p is 1, 2 or 3; preferably p is 2 or 3; or
a N-comprising 7-membered heterocycle optionally substituted by an alkyl and p is 1, 2 or 4, preferably p is 2;
where R and R', identical or different are independently chosen from H, alkyl, aryl, -alkylaryl,
when each T', identical or different, is independently chosen from H or a linear or branched alkyl, wherein the alkyl is optionally substituted by one or more OR, aryl, and at least one of the T' is different from H,
Ra and Rb, identical or different, are independently chosen from H, alkyl, aryl or arylalkyl, wherein said aryl is optionally substituted by halogen, alkyl, CN, CF$_3$, =O, OR, NRR', COR, COOR, CONRR'; and p is an integer chosen from 0 to 6; preferably Ra and Rb, identical or different, are alkyl and p is 2, 3 or 4, preferably p is 3 or 4; or Ra and Rb together form with the N atom to which they are attached a N comprising 5 to 7-membered heterocycle which may comprise one or two more heteroatoms chosen from N, O or S, said heterocycle being optionally substituted by one or more of halogen; =O; alkyl; -alkylaryl or aryl wherein said aryl is optionally substituted by halogen; CN; CF$_3$; OR; NRR'; COR; COOR; CONRR'; and p is an integer chosen from 0 to 6; preferably Ra and Rb form with the N atom to which they are attached a N-comprising 5-membered heterocycle and p is 2, 3 or 4;

where R and R', identical or different are independently chosen from H, alkyl, aryl, -alkylaryl,

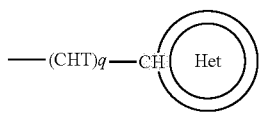

wherein:

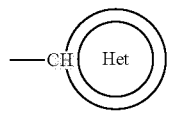

is a saturated monocyclic 5-membered heterocycle comprising a nitrogen atom and substituted by an alkyl, provided that the alkyl is not an ethyl; -alkylaryl; OR; C(=O)OR; =O; CN; CF$_3$; COR; NRR'; CONRR'; aryl; wherein said aryl is optionally substituted by alkyl, halogen, OR, COR or NR'R; or a monocyclic 6 membered heterocycle comprising an nitrogen atom and optionally substituted by one or more of -alkylaryl, OR; C(=O)OR; =O; CN; CF$_3$; COR; NRR'; CONRR'; aryl; wherein said aryl is optionally substituted by halogen, COR, OR or NR'R;

q is an integer chosen from 0 to 6; preferably 0, 1 or 2; preferably 1 or 2;

each T, identical or different is independently chosen from H or alkyl;

where R and R', identical or different are independently chosen from H, alkyl, aryl, -alkylaryl; preferably alkyl;

preferably

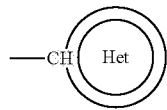

is a pyrrolidine or a piperidine optionally substituted by methyl, -alkylaryl, where aryl is optionally substituted by halogen, COR, OR or NR'R, preferably by OR or NR'R; q is 1 or 2, T is identical or different is independently chosen from H or alkyl and R and R', identical or different are independently chosen from H, alkyl, aryl, -alkylaryl; preferably alkyl;

or X and Y together form with the N atom to which they are attached an heterocycle, preferably a 6- or 7-membered heterocycle; comprising said N atom and optionally one or two more heteroatoms, preferably one more nitrogen; said heterocyle is optionally insaturated and/or is optionally substituted by one or more heterocycle or -alkylheterocycle said heterocycle, comprising one or two heteroatom, preferably nitrogen, and being optionally substituted by an alkyl;

preferably the heterocycle is a 6-membered heterocycle optionally comprising one more nitrogen, and optionally insaturated and/or optionally substituted by one or more heterocycle; -alkylheterocycle said heterocycle, comprising one or two heteroatom, preferably nitrogen, being optionally substituted by an alkyl; or a tautomer thereof, and/or a pharmaceutically acceptable salt thereof.

According a specific embodiment, those compounds of formula (I) are chosen from:

9-Chloro-5,6,7,8-tetrahydro-acridine-3-carboxylic acid [1-(3-methyl-benzyl)-piperidin-4-ylmethyl]-amide 9-Chloro-5,6,7,8-tetrahydro-acridine-3-carboxylic acid (1-ethyl-pyrrolidin-2-ylmethyl)-amide 9-Chloro-5,6,7,8-tetrahydro-acridine-3-carboxylic acid (2-dipropylamino-ethyl)-amide 9-Chloro-5,6,7,8-tetrahydro-acridine-3-carboxylic acid [2-(butyl-ethyl-amino)-ethyl]-amide 9-Chloro-5,6,7,8-tetrahydro-acridine-3-carboxylic acid [3-(benzyl-ethyl-amino)-propyl]-amide 9-Chloro-5,6,7,8-tetrahydro-acridine-3-carboxylic acid (3-dipropylamino-propyl)-amide 9-Chloro-5,6,7,8-tetrahydro-acridine-3-carboxylic acid (2-diethylamino-ethyl)-amide 9-Chloro-5,6,7,8-tetrahydro-acridine-3-carboxylic acid (3-pyrrolidin-1-yl-propyl)-amide 9-Chloro-5,6,7,8-tetrahydro-acridine-3-carboxylic acid [3-(2,6-dimethyl-piperidin-1-yl)-propyl]-amide 9-Chloro-5,6,7,8-tetrahydro-acridine-3-carboxylic acid (3-diethylamino-propyl)-amide 9-Chloro-5,6,7,8-tetrahydro-acridine-3-carboxylic acid (2-dimethylamino-ethyl)-amide Azepan-1-yl-(9-chloro-5,6,7,8-tetrahydro-acridin-3-yl)-methanone 9-Chloro-5,6,7,8-tetrahydro-acridine-3-carboxylic acid [3-(4-propyl-piperazin-1-yl)-propyl]-amide 9-Chloro-5,6,7,8-tetrahydro-acridine-3-carboxylic acid [3-(benzyl-methyl-amino)-propyl]-amide 9-Chloro-5,6,7,8-tetrahydro-acridine-3-carboxylic acid [3-(4-methyl-piperazin-1-yl)-propyl]-amide

[1,4']Bipiperidinyl-1'-yl-(9-chloro-5,6,7,8-tetrahydro-acridin-3-yl)-methanone

9-Chloro-5,6,7,8-tetrahydro-acridine-3-carboxylic acid (3-morpholin-4-yl-propyl)-amide 9-chloro-N-(3-(2-methylpiperidin-1-yl)propyl)-5,6,7,8-tetrahydroacridine-3-carboxamide 9-chloro-N-(2-(1-methylpyrrolidin-2-yl)ethyl)-5,6,7,8-tetrahydroacridine-3-carboxamide 9-chloro-N-(3-(pyrrolidin-1-ylmethyl)benzyl)-5,6,7,8-tetrahydroacridine-3-carboxamide 9-chloro-N-(3-(pyrrolidin-1-ylmethyl)phenyl)-5,6,7,8-tetrahydroacridine-3-carboxamide 9-chloro-N-(4-(pyrrolidin-1-ylmethyl)benzyl)-5,6,7,8-tetrahydroacridine-3-carboxamide 9-chloro-N-((1-(4-methoxybenzyl)piperidin-4-yl)methyl)-5,6,7,8-tetrahydroacridine-3-carboxamide 9-chloro-N-((1-4-N,N-dimethylbenzyl)piperidin-4-yl)methyl)-5,6,7,8-tetrahydroacridine-3-carboxamide 9-chloro-N-((piperidin-4-yl)methyl)-5,6,7,8-tetrahydroacridine-3-carboxamide 9-chloro-N-(3-hydroxy-3-phenyl-2-pyrrolidin-1-ylmethyl-propyl)-5,6,7,8-tetrahydroacridine-3-carboxamide
N-(2-(azepan-1-yl)ethyl)-9-chloro-5,6,7,8-tetrahydroacridine-3-carboxamide
9-chloro-N-(2-(piperidin-1-yl)ethyl)-5,6,7,8-tetrahydroacridine-3-carboxamide
(9-chloro-5,6,7,8-tetrahydroacridine-3-yl)(4-((1-methylpiperidin-4-yl)methyl)piperazin-1-yl)methanone
(9-chloro-5,6,7,8-tetrahydroacridine-3-yl)(4-(1-methylpiperidin-4-yl)piperazin-1-yl)methanone
(9-chloro-5,6,7,8-tetrahydroacridine-3-yl)(piperidin-1-yl)methanone
N-((1-benzylpiperidin-4-yl)methyl)-9-chloro-5,6,7,8-tetrahydroacridine-3-carboxamide
9-chloro-N-((1-(3-phenylpropyl)piperidin-4-yl)methyl)-5,6,7,8-tetrahydroacridine-3-carboxamide
9-chloro-N-((1-phenethylpiperidin-4-yl)methyl)-5,6,7,8-tetrahydroacridine-3-carboxamide
9-chloro-N-(5-(diethylamino)pentan-2-yl)-5,6,7,8-tetrahydroacridine-3-carboxamide
(R)-9-chloro-N-((1-ethylpyrrolidin-2-yl)methyl)-5,6,7,8-tetrahydroacridine-3-carboxamide
(S)-9-chloro-N-((1-ethylpyrrolidin-2-yl)methyl)-5,6,7,8-tetrahydroacridine-3-carboxamide
9-chloro-N-(3-(dimethylamino)-2,2-dimethylpropyl)-5,6,7,8-tetrahydroacridine-3-carboxamide
9-chloro-N-(3-(3,4-dihydroisoquinolin-2(1H)-yl)propyl)-5,6,7,8-tetrahydroacridine-3-carboxamide
Chlorhydrate of 9-chloro-5,6,7,8-tetrahydroacridine-3-carboxylic acid (2-diethylamino-ethyl)amide
or a tautomer thereof, and/or a pharmaceutically acceptable salt thereof.
Preferably the invention concerns the following compounds:
9-chloro-N-(3-(2-methylpiperidin-1-yl)propyl)-5,6,7,8-tetrahydroacridine-3-carboxamide
9-chloro-N-(2-(1-methylpyrrolidin-2-yl)ethyl)-5,6,7,8-tetrahydroacridine-3-carboxamide
9-chloro-N-(3-(pyrrolidin-1-ylmethyl)benzyl)-5,6,7,8-tetrahydroacridine-3-carboxamide
9-chloro-N-(3-(pyrrolidin-1-ylmethyl)phenyl)-5,6,7,8-tetrahydroacridine-3-carboxamide
9-chloro-N-(4-(pyrrolidin-1-ylmethyl)benzyl)-5,6,7,8-tetrahydroacridine-3-carboxamide
9-chloro-N-((1-(4-methoxybenzyl)piperidin-4-yl)methyl)-5,6,7,8-tetrahydroacridine-3-carboxamide
9-chloro-N-((1-4-N,N-dimethylbenzyl)piperidin-4-yl)methyl)-5,6,7,8-tetrahydroacridine-3-carboxamide
9-chloro-N-((piperidin-4-yl)methyl)-5,6,7,8-tetrahydroacridine-3-carboxamide
9-chloro-N-(3-hydroxy-3-phenyl-2-pyrrolidin-1-ylmethyl-propyl)-5,6,7,8-tetrahydroacridine-3-carboxamide
9-Chloro-5,6,7,8-tetrahydro-acridine-3-carboxylic acid (3-pyrrolidin-1-yl-propyl)-amide
Azepan-1-yl-(9-chloro-5,6,7,8-tetrahydro-acridin-3-yl)-methanone
[1,4']Bipiperidinyl-1'-yl-(9-chloro-5,6,7,8-tetrahydro-acridin-3-yl)-methanone
N-(2-(azepan-1-yl)ethyl)-9-chloro-5,6,7,8-tetrahydroacridine-3-carboxamide
9-chloro-N-(2-(piperidin-1-yl)ethyl)-5,6,7,8-1etranydroacridine-3-carboxamide
(9-chloro-5,6,7,8-tetrahydroacridin-3-yl)(4-((1-methylpiperidin-4-yl)methyl)piperazin-1-yl)methanone
(9-chloro-5,6,7,8-tetrahydroacridin-3-yl)(4-(1-methylpiperidin-4-yl)piperazin-1-yl)methanone
(9-chloro-5,6,7,8-tetrahydroacridin-3-yl)(piperidin-1-yl)methanone
N-((1-benzylpiperidin-4-yl)methyl)-9-chloro-5,6,7,8-tetrahydroacridine-3-carboxamide
9-chloro-N-((1-(3-phenylpropyl)piperidin-4-yl)methyl)-5,6,7,8-tetrahydroacridine-3-carboxamide
9-chloro-N-((1-phenethylpiperidin-4-yl)methyl)-5,6,7,8-tetrahydroacridine-3-carboxamide
9-chloro-N-(5-(diethylamino)pentan-2-yl)-5,6,7,8-tetrahydroacridine-3-carboxamide
(R)-9-chloro-N-((1-ethylpyrrolidin-2-yl)methyl)-5,6,7,8-tetrahydroacridine-3-carboxamide
(S)-9-chloro-N-((1-ethylpyrrolidin-2-yl)methyl)-5,6,7,8-tetrahydroacridine-3-carboxamide
9-chloro-N-(3-(dimethylamino)-2,2-dimethylpropyl)-5,6,7,8-tetrahydroacridine-3-carboxamide;
Chlorhydrate of 9-chloro-5,6,7,8-tetrahydroacridine-3-carboxylic acid (2-diethylamino-ethyl)amide
or a tautomer thereof, and/or a pharmaceutically acceptable salt thereof.
Preferably the invention concerns the following compounds:
9-chloro-N-(3-(2-methylpiperidin-1-yl)propyl)-5,6,7,8-tetrahydroacridine-3-carboxamide
9-chloro-N-(2-(1-methylpyrrolidin-2-yl)ethyl)-5,6,7,8-tetrahydroacridine-3-carboxamide
9-chloro-N-(3-(pyrrolidin-1-ylmethyl)benzyl)-5,6,7,8-tetrahydroacridine-3-carboxamide
9-chloro-N-(3-(pyrrolidin-1-ylmethyl)phenyl)-5,6,7,8-tetrahydroacridine-3-carboxamide
9-chloro-N-(4-(pyrrolidin-1-ylmethyl)benzyl)-5,6,7,8-tetrahydroacridine-3-carboxamide
9-chloro-N-((1-(4-methoxybenzyl)piperidin-4-yl)methyl)-5,6,7,8-tetrahydroacridine-3-carboxamide
9-chloro-N-((1-4-N,N-dimethylbenzyl)piperidin-4-yl)methyl)-5,6,7,8-tetrahydroacridine-3-carboxamide
9-chloro-N-((piperidin-4-yl)methyl)-5,6,7,8-tetrahydroacridine-3-carboxamide
9-chloro-N-(3-hydroxy-3-phenyl-2-pyrrolidin-1-ylmethyl-propyl)-5,6,7,8-tetrahydroacridine-3-carboxamide
9-Chloro-5,6,7,8-tetrahydro-acridine-3-carboxylic acid (3-pyrrolidin-1-yl-propyl)-amide
Azepan-1-yl-(9-chloro-5,6,7,8-tetrahydro-acridin-3-yl)-methanone
[1,4']Bipiperidinyl-1'-yl-(9-chloro-5,6,7,8-tetrahydro-acridin-3-yl)-methanone
N-(2-(azepan-1-yl)ethyl)-9-chloro-5,6,7,8-tetrahydroacridine-3-carboxamide
9-chloro-N-(2-(piperidin-1-yl)ethyl)-5,6,7,8-1etranydroacridine-3-carboxamide
(9-chloro-5,6,7,8-tetrahydroacridin-3-yl)(4-((1-methylpiperidin-4-yl)methyl)piperazin-1-yl)methanone
(9-chloro-5,6,7,8-tetrahydroacridin-3-yl)(4-(1-methylpiperidin-4-yl)piperazin-1-yl)methanone
(9-chloro-5,6,7,8-tetrahydroacridin-3-yl)(piperidin-1-yl)methanone
N-((1-benzylpiperidin-4-yl)methyl)-9-chloro-5,6,7,8-tetrahydroacridine-3-carboxamide
9-chloro-N-((1-(3-phenylpropyl)piperidin-4-yl)methyl)-5,6,7,8-tetrahydroacridine-3-carboxamide
9-chloro-N-((1-phenethylpiperidin-4-yl)methyl)-5,6,7,8-tetrahydroacridine-3-carboxamide
9-chloro-N-(5-(diethylamino)pentan-2-yl)-5,6,7,8-tetrahydroacridine-3-carboxamide
9-chloro-N-(3-(dimethylamino)-2,2-dimethylpropyl)-5,6,7,8-tetrahydroacridine-3-carboxamide
Chlorhydrate of 9-chloro-5,6,7,8-tetrahydroacridine-3-carboxylic acid (2-diethylamino-ethyl)amide
or a tautomer thereof, and/or a pharmaceutically acceptable salt thereof.

As used hereabove or hereafter:

"Alkyl" means an aliphatic hydrocarbon group which may be straight or branched having 1 to 20 carbon atoms in the chain. Preferred alkyl groups have 1 to 12 carbon atoms in the chain. "Branched" means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl.

As used herein, the term "cycloalkyl" refers to an aromatic or non aromatic hydrocarbon mono, bi or multi cyclic ring of 3 to 10 carbon atoms formed by the removal of one hydrogen atom. A designation such as "$C_5$-$C_7$ cycloalkyl" refers to a cycloalkyl radical containing from 5 to 7 carbon atoms. Examples include cyclopropyl, cyclopentyl, cyclohexyl, cycloheptyl, adamantyl, etc. as well as the systems formed by their condensation or by the condensation with a phenyl group.

"Alken" means an aliphatic hydrocarbon group containing a carbon-carbon double bond and which may be straight or branched having 2 to 15 carbon atoms in the chain. Preferred alkenyl groups have 2 to 12 carbon atoms in the chain; and more preferably about 2 to 4 carbon atoms in the chain. Exemplary alkenyl groups include ethenyl, propenyl, n-butenyl, i-butenyl, 3-methylbut-2-enyl, n-pentenyl, heptenyl, octenyl, nonenyl, decenyl.

"Halogen atom" refers to fluorine, chlorine, bromine or iodine atom; preferably fluorine and chlorine atom.

"Perhalogenoalkyl" refers to an alkyl group as defined above where all H atoms are replaced by halogen atoms.

"Polyhalogenoalkyl" refers to an alkyl group as defined above where one or more H atoms are replaced by halogen atoms.

"Aryl" means an aromatic monocyclic or multicyclic hydrocarbon ring system of 6 to 14 carbon atoms, preferably of 6 to 10 carbon atoms. Exemplary aryl groups include phenyl or naphthyl.

As used herein, the terms "heterocycle" or "heterocyclic" refer to a saturated, partially unsaturated or unsaturated, non aromatic stable 3 to 14, preferably 5 to 10-membered mono, bi or multicyclic rings wherein at least one member of the ring is a hetero atom. Typically, heteroatoms include, but are not limited to, oxygen, nitrogen, sulfur, selenium, and phosphorus atoms. Preferable heteroatoms are oxygen, nitrogen and sulfur.

Suitable heterocycles are also disclosed in *The Handbook of Chemistry and Physics,* 76$^{th}$ Edition, CRC Press, Inc., 1995-1996, p. 2-25 to 2-26, the disclosure of which is hereby incorporated by reference.

Preferred non aromatic heterocyclic include, but are not limited to pyrrolidinyl, pyrazolidinyl, imidazolidinyl, oxiranyl, tetrahydrofuranyl, dioxolanyl, tetrahydro-pyranyl, dioxanyl, dioxolanyl, piperidyl, piperazinyl, morpholinyl, pyranyl, imidazolinyl, pyrrolinyl, pyrazolinyl, thiazolidinyl, tetrahydrothiopyranyl, dithianyl, thiomorpholinyl, dihydropyranyl, tetrahydropyranyl, dihydropyranyl, tetrahydro-pyridyl, dihydropyridyl, tetrahydropyrinidinyl, dihydrothiopyranyl, azepanyl, as well as the fused systems resulting from the condensation with a phenyl group.

As used herein, the term "heteroaryl" or aromatic heterocycles refers to a 5 to 14, preferably 5 to 10-membered aromatic hetero, mono-, bi- or multicyclic ring. Examples include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2, 4-thiadiazolyl, isothiazolyl, triazoyl, tetrazolyl, isoquinolyl, benzothienyl, isobenzofuryl, pyrazolyl, carbazolyl, benzimidazolyl, isoxazolyl, pyridyl-N-oxide, as well as the fused systems resulting from the condensation with a phenyl group.

"Alkyl", "alkenyl", "cycloalkyl", "aryl", "heteroaryl", "heterocycle" and the likes refers also to the corresponding "alkylene", "alkenylene", "cycloalkylene", "arylene", "heteroarylene", "heterocyclene" and the likes which are formed by the removal of two hydrogen atoms.

As used herein, the term "patient" refers to either an animal, such as a valuable animal for breeding, company or preservation purposes, or preferably a human or a human child, which is afflicted with, or has the potential to be afflicted with one or more diseases and conditions described herein.

As used herein, a "therapeutically effective amount" refers to an amount of a compound of the present invention which is effective in preventing, reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

As used herein, the expression "pharmaceutically acceptable" refers to those compounds, materials, excipients, compositions or dosage forms which are, within the scope of sound medical judgment, suitable for contact with the tissues of human beings and animals without excessive toxicity, irritation, allergic response or other problem complications commensurate with a reasonable benefit/risk ratio.

As used herein, "pharmaceutically acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like, including mono, di or tri-salts thereof; and the salts prepared from organic acids such as acetic, propionic, succinic, tartaric, citric, methanesulfonic, benzenesulfonic, glucoronic, glutamic, benzoic, salicylic, toluenesulfonic, oxalic, fumaric, maleic, lactic and the like. Further addition salts include ammonium salts such as tromethamine, meglumine, epolamine, etc., metal salts such as sodium, potassium, calcium, zinc or magnesium.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences,* 20$^{th}$ ed., Mack Publishing Company, Easton, Pa., 2000, the disclosure of which is hereby incorporated by reference.

The compounds of the general formula (I) having geometrical and stereoisomers are also a part of the invention.

According to a further object, the present invention is also concerned with the process of preparation of the compounds of formula (I).

The compounds and process of the present invention may be prepared in a number of ways well-known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art.

In particular, such methods can be found in R. C. Larock, *Comprehensive Organic Transformations*, Wiley-VCH Publishers, 1999.

It will be appreciated that the compounds of the present invention may contain one or more asymmetrically substituted carbon atoms, and may be isolated in optically active or racemic forms. Thus, all chiral, diastereomeric, racemic forms, isomeric forms of a structure are intended, unless the specific stereochemistry or isomeric form is specifically indicated. It is well-known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Additionally, the process of the invention may lead to several regioisomers which are all encompassed by the present invention. Regioisomers are generally isolated by chromatography.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxyl, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, 3$^{rd}$ ed., John Wiley and Sons, 1999; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethylformamide; alcohols such as ethanol and methanol and ethers, such as diethyl ether and tetrahydrofuran.

The reactions can take place over a wide range of temperatures. In general, it is found convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary, after distilling off the solvent from the reaction mixture, pouring the residue into water followed by extraction with a water-immiscible organic solvent and distilling off the solvent from the extract. Additionally, the product can, if desired, be further purified by various well-known techniques, such as recrystallization, reprecipitation or the various chromatography techniques, notably column chromatography or preparative thin layer chromatography.

The process of preparation of a compound of formula (I) of the invention is a further object of the present invention.

According to a first aspect, a compound of the invention of formula (I) can be obtained by reacting a corresponding compound of formula (VII):

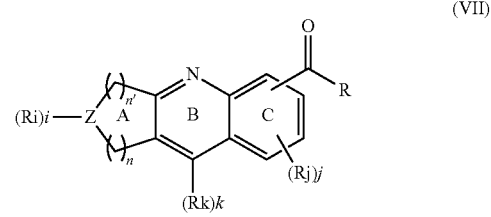

(VII)

by peptidic coupling
with a corresponding compound of formula (VIII):

(VIII)

where i, j, k, n, Z, Ri, Rj and Rk are defined as in formula (I), R is OH or a halogen and X' and Y' are identical to X and Y respectively, or a precursor thereof, or an amino protecting group, optionally followed by alkylation(s) or deprotection as the case may be, respectively.

Said compound of formula (VII) may be obtained by a corresponding compound of formula (VI):

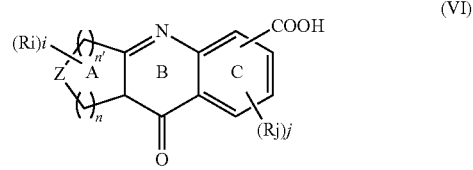

(VI)

where i, j, n, Z, Ri, Rj are defined as in formula (I), by functionalization, i.e. the Rk group is introduced via convenient functionalization of the keto group which include halogenations, reduction then dehydration, nucleophilic addition followed by dehydration. In particular to introduce Rk=Hal, this functionalization comprises the steps of halogenations, reduction then deshydratation.

The present invention also concerns compound of formula (VI):

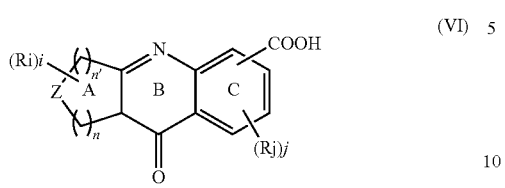

(VI)

where i, j, n, Z, Ri, Rj are defined as in formula (I), with the exception of:

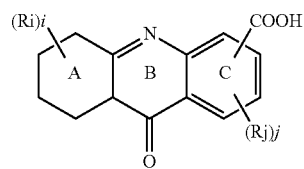

The compound of formula (VI) may be obtained by coupling compounds (II) and (III) or (IV) and (V) according to either of the two pathways below.

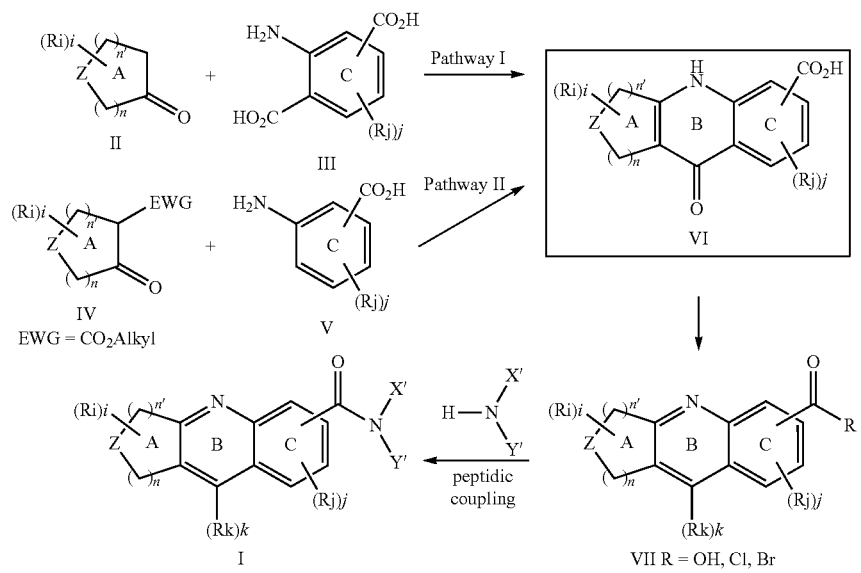

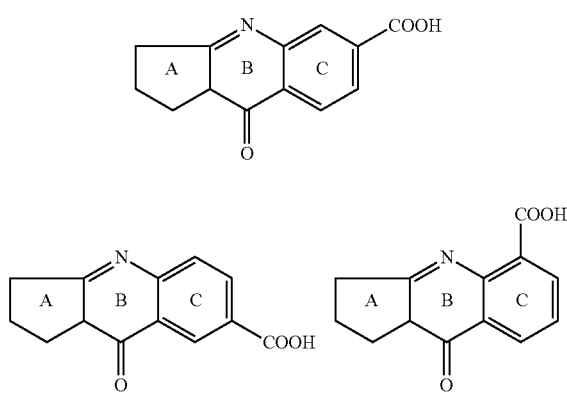

According to a particular embodiment, compounds of formula (VI) are the following compounds:

First, a condensation between ketones (II) or substituted ketones (IV) is performed with a substituted aniline (III) or (V) leading to the tricyclic acids (VI). Amino terephthalic acids (III) or (V) and the corresponding ketones (II) (pathway I) or (IV) (pathway II) are mixed and stirred in the appropriate solvent. Depending on the reactivity, mixture can be heated or catalysed by the use of acidic conditions. In the case of pathway (II), the reaction is performed via the cyclisation of an intermediate enamine of (IV) and (V).

Further, functionalization of (VI) affords compounds (VII) as acyl halides or carboxylic acids. Peptidic coupling is performed using standard conditions depending on the nature of (VII). Amines HNXY can be either be commercially available or prepared using classical methods prior to coupling to compounds (VII).

An alternative approach was used in the case where —NXY is a diamine. It include the coupling of compounds (VII) with mono-protected—secondary or primary—amines precursor followed by deprotection and one or two successive alkylations using electrophilic reagents such as halides derivatives or aldehydes.

The term "precursor" is used herein to refer to compounds which differ from the indicated or desired compounds by the presence and/or absence of groups or functions. Such groups or functions may be introduced, transformed and/or omitted by common functionalization reactions, known from the skilled person.

The functionalization reaction may be carried out by application or adaptation of known methods.

The above reactions can be carried out by the skilled person by applying or adapting the methods illustrated in the examples hereinafter.

Further, the process of the invention may also comprise the additional step of isolating the compound of formula (I). This can be done by the skilled person by any of the known conventional means, such as the recovery methods described above.

Generally, the starting products (II), (Ill), (IV), (V) and (VIII) are commercially available mainly from Aldrich or Acros or other typical chemicals supplier or may be obtained by applying or adapting any known methods or those described in the examples.

According to a further object, the present invention concerns also the pharmaceutical compositions comprising a compound of formula (I) as defined above or a tautomer thereof and/or its pharmaceutically acceptable salts, with a pharmaceutically acceptable excipient.

Preferred embodiments of formula (I) are as defined above in respect of the compounds of the invention.

According to a still further object, the present invention concerns a compound of formula (I) of the invention for inhibiting cysteine protease.

The compounds of the invention are useful for inhibiting cysteine proteases, in particular specific de-ubiquitination enzymes such as USPs, and more particularly USP-7 in patients in the need thereof.

The compounds of the invention are particularly useful for treating and/or preventing cancer and metastasis, more particularly prostate and/or colon cancers, neurodegenerative diseases, such as Alzheimer's disease and Parkinson's disease, immunological disorders, bone and joint diseases, osteoporosis, arthritis inflammatory disorders, cardiovascular diseases, viral infections and diseases, and/or viral infectivity and/or latency, bacterial infections and diseases.

In particular, said viral infections and diseases are chosen from herpes simplex-1 or -2 viral infections, hepatitis A, hepatitis C, SARS coronavirus infection and disease, Epstein-Barr virus, rhinoviral infections and diseases, adenoviral infections and diseases, poliomyelitis.

According to an aspect, said compounds inhibit one or more viral cysteine proteases.

Bacterial cysteine proteases may be chosen from streptopain, clostripain, staphylococcal cysteine protease, gingipain.

The present invention also concerns the combinations comprising a compound of formula (I) as defined in the claims or a tautomer thereof, and/or a pharmaceutically acceptable salt thereof, with one or more active agents chosen from anti-cancer agents, neurological agents, thrombolytic agents, antioxidant agents. anti-infective, anti-hypertensive agents, diuretic agents, thrombolytic agents, immunosuppressive agents, cardiovascular agents, immunomodulatory agents, anti-inflammatory agents, antiviral agents, anti-bacterial agents.

The present invention also concerns the corresponding methods of treatment comprising the administration of a compound of the invention together with a pharmaceutically acceptable carrier or excipient to a patient in the need thereof.

The identification of those subjects who are in need of treatment of herein-described diseases and conditions is well within the ability and knowledge of one skilled in the art. A veterinarian or a physician skilled in the art can readily identify, by the use of clinical tests, physical examination, medical/family history or biological and diagnostic tests, those subjects who are in need of such treatment.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of a compound of formula (I), which is required to achieve the desired biological effect, will vary depending upon a number of factors, including the chemical characteristics (e.g. hydrophobicity) of the compounds employed, the potency of the compounds, the type of disease, the species to which the patient belongs, the diseased state of the patient, the route of administration, the bioavailability of the compound by the chosen route, all factors which dictate the required dose amounts, delivery and regimen to be administered.

"Pharmaceutically" or "pharmaceutically acceptable" refer to molecular entities and compositions that do not produce an adverse, allergic or other untoward reaction when administered to an animal, or a human, as appropriate.

As used herein, "pharmaceutically acceptable excipient" includes any carriers, diluents, adjuvants, or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well-known in the art. Except insofar as any conventional media or agent is incompatible with the active ingredient, its use in the therapeutic compositions is contemplated. Supplementary active ingredients can also be incorporated into the compositions as suitable therapeutic combinations.

In the context of the invention, the term "treating" or "treatment", as used herein, means reversing, alleviating, inhibiting the progress of, or preventing the disorder or condition to which such term applies, or one or more symptoms of such disorder or condition.

"Therapeutically effective amount" means an amount of a compound/medicament according to the present invention effective in preventing or treating a pathological condition requiring the inhibition of an active cysteine protease involved in its pathogenesis.

According to the invention, the terms "patient" or "patient in need thereof", are intended for an animal or a human being affected or likely to be affected with a pathological condition involving an active cysteine protease in its pathogenesis. Preferably, the patient is human.

In general terms, the compounds of this invention may be provided in an aqueous physiological buffer solution containing 0.1 to 10% w/v compound for parenteral administration. Typical dose ranges are from 1 µg/kg to 0.1 g/kg of body weight per day; a preferred dose range is from 0.01 mg/kg to 100 mg/kg of body weight per day or an equivalent dose in a human child. The preferred dosage of drug to be administered is likely to depend on such variables as the type and extent of progression of the disease or disorder, the overall health status of the particular patient, the relative biological efficacy of the compound selected, the formulation of the compound, the route of administration (intravenous, intramuscular, or other), the pharmacokinetic properties of the compound by the chosen delivery route, and the speed (bolus or continuous infusion) and schedule of administrations (number of repetitions in a given period of time).

The compounds of the present invention are also capable of being administered in unit dose forms, wherein the expression "unit dose" means a single dose which is capable of being administered to a patient, and which can be readily handled and packaged, remaining as a physically and chemically stable unit dose comprising either the active compound itself, or as a pharmaceutically acceptable composition, as described hereinafter. As such, typical total daily dose ranges are from 0.01 to 100 mg/kg of body weight. By way of general guidance, unit doses for humans range from 1 mg to 3000 mg per day. Preferably, the unit dose range is from 1 to 500 mg administered one to six times a day, and even more preferably from 10 mg to 500 mg, once a day. Compounds provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasally, particularly in the form of powders, nasal drops, or aerosols; or dermally, for example, topically in ointments, creams, lotions, gels or sprays, or via trans-dermal patches.

The compositions may conveniently be administered in unit dosage form and may be prepared by any of the methods well-known in the pharmaceutical art, for example, as described in *Remington: The Science and Practice of Pharmacy*, 20$^{th}$ ed.; Gennaro, A. R., Ed.; Lippincott Williams & Wilkins: Philadelphia, Pa., 2000.

Preferred formulations include pharmaceutical compositions in which a compound of the present invention is formulated for oral or parenteral administration.

For oral administration, tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal. Preferred tablets contain lactose, cornstarch, magnesium silicate, croscarmellose sodium, povidone, magnesium stearate, or talc in any combination.

Liquid preparations for parenteral administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringers dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

The invention is further illustrated but not restricted by the description in the following examples and figures as a non limiting illustration for selective inhibition of USP7 deubiquitinating activity over a panel of active DUBs in physiological conditions.

BRIEF DESCRIPTION OF THE DRAWINGS

FIG. 1A shows the C-terminally modified vinyl sulfone derivative of ubiquitin (HA-Ub-VS), which binds covalently to the cysteine active site of deubiquitinating enzymes.

FIG. 1B shows that the labeling of FIG. 1A followed by immunoblot with the anti-HA antibody allowed the identification of all active deubiquitinating enzymes from HCT116 cell lysates. In addition, active USP7 was identified in this assay as indicated by the mobility shift observed following immunoblot with anti-USP7 antibody. This labeling, specific to the active form of DUBs, is inhibited by a thiol-reactive compound (NEM) in a non-specific manner.

FIG. 4A shows HCT116 cells were next treated either with different doses of compounds of examples 14 and 5 or with Doxycycline to induce USP7 silencing. Localization of the HA-Ub-VS-USP7 protein was facilitated by the specific silencing of USP7 as indicated in the presence of doxycycline (FIG. 4A, +Dox). Once this band identified, cell lysates were treated with different doses of compounds of examples 14 and 5 and a specific and dose-dependent decrease of the HA-Ub-VS-USP7 protein level was clearly observed (FIGS. 4A and B).

FIG. 4B shows that once this band of FIG. 4A is identified, cell lysates were treated with different doses of compounds of examples 14 and 5 and a specific and dose-dependent decrease of the HA-Ub-VS-USP7 protein level was clearly observed. This effect on USP7 activity was confirmed with anti-USP7 antibody as indicated by the mobility shift observed between the treated and non-treated samples in this Figure.

FIGS. 5A and 5B show confirmation of the findings of FIGS. 4A and 4B in cell lysates prepared from HEK293 cells. These results thus demonstrate that different compounds from this new chemical series (compounds of examples 14 and 5) inhibit specifically and dose-dependently USP7 deubiquitinating activity over a panel of active DUBs in physiological conditions.

DETAILED DESCRIPTION OF THE INVENTION

Figure 2B:
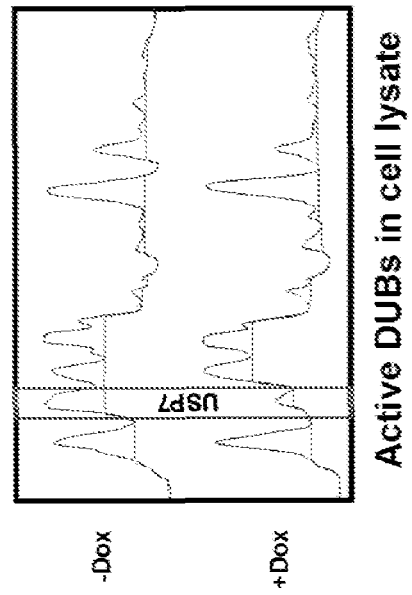
FIG. 2B shows a quantification showing the specific decrease of FIG. 2A (quantification performed using the image analysis software, GeneTools, Syngene). USP7 silencing induced by Doxycycline treatment was confirmed with anti-USP7 antibody.

Representative compounds of the invention can be synthesized according to the following procedures.

General Analytical Procedures

NMR spectra were recorded at 300 or 400 MHz for $^1$H and at 75 or 100, MHz for $^{13}$C on a Bruker or Varian spectrometer with CDCl$_3$ or DMSO-d$_6$ as solvent. The chemical shifts are given in ppm, referenced to the internal TMS or deuterated solvent signal.

LC-MS analysis was used to analyze and purify target compounds. LC-MS analyses were performed using an Waters Micromass, Bruker Esquire 3000 (ESI-IT) or Agilent Iontrap XCT-Plus mass spectrometers and Waters Alliance 2790 or Agilent 1100 Series LC systems with UV and/or DAD detection. Columns: Waters XTerra MS C18, 30×2.1 mm (3.5 μm), Atlantis T3 C18, 3 μm, 50 mm×2.1 mm or Inertsil C8, 250 mm, 4.6 mm, 5 μm. Flow rates: 0.8-1.2 ml/min, Gradients: a) water 10% MeOH, ammonium formate 10 mM, to 100% MeOH or b) 95% Water-acetonitrile, 0.1% HCOOH to 95% acetonitrile). UV detection: 190 to 400 nm. All compounds were >95% pure.

General Procedure 1

Preparation of Compounds (VII)

Preparation of the Intermediate of Formula (VIIa)

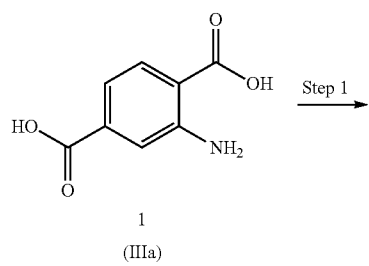

(IIIa)

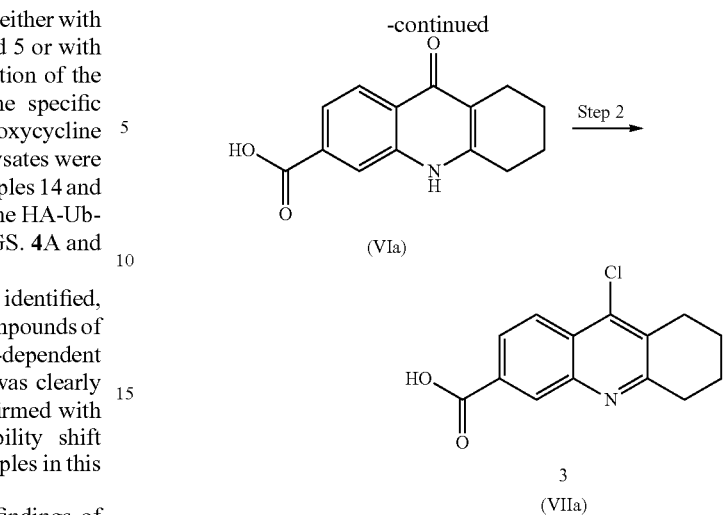

Step 1: Condensation 9-oxo-5,6,7,8,9,10-hexahydro-acridine-3-carboxylic acid (VIa)

To a suspension of 2-amino terephthalic acid (12 g, 6.6 mmols) in diphenyl ether (120 mL), cyclohexanone (25 mL) was added and the reaction mixture was heated to 250° C. for 10 min. Reaction completion was monitored by LC/MS (75% starting material and 25% Product formation was observed). Cyclohexanone (25 mL) was added and the reaction mixture was heated to 250° C. for another 10 min. (LC/MS showed 50% product formation). The above process was repeated till LC/MS showed complete product formation (Starting material <2%). The reaction mixture was cooled to 25° C., product was filtered, washed with hexane (100 mL) and dried under vacuum to get 15.8 g of (Via) (98%) as a yellow solid.

$^1$H NMR (300 MHz, DMSO) δ 13.27 (s, 1H), 11.54 (s, 1H), 8.14-8.11 (d, 2H, J=8.4 Hz), 7.72-7.70 (m, 1H), 2.72 (m, 2H), 2.44 (m, 2H), 1.76-1.72 (m, 4H).

MS: calcd for C$_{14}$H$_{13}$NO$_3$, 243.09. found 243.8 (M+H)$^+$.

Step 2: Halogenation 9-chloro-5,6,7,8-tetrahydroacridine-3-carboxylic acid (VIIa)

A suspension of 9-oxo-5,6,7,8,9,10-hexahydro-acridine-3-carboxylic acid (VIa) (10 g, 4.1 mmols) in phosphorous oxychloride (50 mL) was heated to 100° C. for 1 h. Reaction completion was monitored by TLC. After completion, the reaction mixture was cooled to 25° C. and excess phosphorous oxychloride was removed under vacuum. The residue was mixed with ice (50 g) and the pH was adjusted to 4-5 with solid sodium bicarbonate. The solid obtained was filtered, washed with water (250 mL) and dried under vacuum to get 9.6 g (88%) of compound (Vila) as a white solid.

$^1$H NMR (300 MHz, DMSO) δ 13.37 (s, 1H), 8.44 (s, 1H), 8.19-8.16 (d, 1H, J=8.7 Hz), 8.09-8.07 (dd, 1H, J=8.7 Hz, 1.5 Hz), 3.06 (m, 2H), 2.96 (m, 2H), 1.99-1.89 (m, 4H).

MS: calcd for C$_{14}$H1$_2$ClNO$_2$, 261.06. found 261.8 (M+H)$^+$.

Step 3: Amide Formation

To a 0.1M DMF solution of the heterocyclic acids VII, triethylamine was added (2 equiv.) followed by the corresponding amines (1 equiv.) and coupling agent (TBTU, HATU, OHBT, 1 equiv.). The corresponding mixtures were stirred for 1-12 h at 20° C. Concentrated HCl was added and after 5 min stirring, the mixtures were under vacuum. The crude compounds were extracted with 20 mL d'AcOEt, washed with 10 mL of aqueous 0.5M NaHCO$_3$ solution and 10 mL of water. The organics phase were dried over MgSO4 then evaporated under vacuum. Purification using silicagel (gradient CH$_2$Cl$_2$ CH$_2$Cl$_2$/MeOH 9/1) or preparative LC/MS affords the pure corresponding amides.

Selected data of some of the compounds that were prepared by application or adaptation of the method disclosed above are shown below:

9-Chloro-5,6,7,8-tetrahydro-acridine-3-carboxylic acid [1-(3-methyl-benzyl)-piperidin-4-ylmethyl]-amide (1)

$^1$H NMR (400 MHz, DMSO-d6) δ 8.77 (t, J=5.7 Hz, 1H), 8.47 (d, J=1.8 Hz, 1H), 8.17 (d, J=8.8 Hz, 1H), 8.04 (dd, J=1.7, 8.7 Hz, 1H), 7.36 (s, 1H), 7.18 (t, J=7.5 Hz, 1H), 7.09 (s, 1H), 7.07 (d, J=7.7 Hz, 1H), 7.04 (d, J=7.5 Hz, 1H), 3.38 (s, 2H), 3.32-3.29 (m, 2H), 3.21 (d, J=6.7 Hz, 2H), 3.06 (m, 2H), 2.98 (m, 2H), 2.79 (m, 2H), 2.28 (s, 3H), 1.94-1.84 (m, 6H), 1.69 (s, 1H), 1.66 (s, 1H), 1.63-1.53 (m, 1H), 1.28-1.14 (m, 2H).

MS: calcd for C$_{28}$H$_{32}$ClN$_3$O, 461.22. found 462.17 (M+H)$^+$.

9-Chloro-5,6,7,8-tetrahydro-acridine-3-carboxylic acid [3-(benzyl-ethyl-amino)-propyl]-amide (5)

$^1$H NMR (400 MHz, DMSO-d6) δ 8.72 (t, J=5.6 Hz, 1H), 8.43 (d, J=1.7 Hz, 1H), 8.16 (d, J=8.6 Hz, 1H), 8.02 (dd, J=1.7, 8.8 Hz, 1H), 7.29 (m, 4H), 7.18 (m, 1H), 3.54 (s, 2H), 3.32 (m, 2H), 3.06 (m, 2H), 2.98 (m, 2H), 2.46 (m, 4H), 1.89 (m, J=3.73 Hz, 4H), 1.74 (m, J=7.2 Hz, 2H), 0.97 (t, J=7.1 Hz, 3H).

MS: calcd for C$_{26}$H$_{30}$ClN$_3$O, 435.21. found 436.17 (M+H)$^+$.

9-Chloro-5,6,7,8-tetrahydro-acridine-3-carboxylic acid (3-di propylamino-propyl)-amide (6)

$^1$H NMR (400 MHz, DMSO-d6) δ 8.75 (t, J=5.4 Hz, 1H), 8.45 (d, J=1.8 Hz, 1H), 8.17 (d, J=8.8 Hz, 1H), 8.04 (dd, J=1.8, 8.7 Hz, 1H), 3.37-3.28 (m, 2H), 3.06 (m, 2H), 2.98 (m, 2H), 2.44 (t, J=7.1 Hz, 2H), 2.32 (t, J=7.1 Hz, 4H), 1.9 (m, J=3.7 Hz, 4H), 1.68 (m, J=7.0 Hz, 2H), 1.39 (m, J=7.3 Hz, 4H), 0.83 (t, J=7.3 Hz, 6H).

MS: calcd for C$_{23}$H$_{32}$ClN$_3$O, 401.22. found 402.22 (M+H)$^+$.

9-Chloro-5,6,7,8-tetrahydro-acridine-3-carboxylic acid (2-diethylamino-ethyl)-amide (7)

$^1$H NMR (400 MHz, DMSO-d$_6$): δ (ppm): 8.69 (t, J=5.7 Hz, 1H), 8.44 (d, J=1.8 Hz, 1H), 8.18 (d, J=8.8 Hz, 1H), 8.04 (dd, J=1.8, 8.7 Hz, 1H), 3.41-3.28 (m, 2H), 3.06 (m, 2H), 2.98 (m, 2H), 2.59 (dd, J=6.8, 8.2 Hz, 2H), 2.52 (q, J=7.1 Hz, 2H), 1.9 (m, J=3.7 Hz, 4H), 0.98 (t, J=7.1 Hz, 6H)

MS: calcd for C$_{21}$H$_{26}$ClN$_3$O, 359.18. found 360.19 (M+H)$^+$.

9-Chloro-5,6,7,8-tetrahydro-acridine-3-carboxylic acid (3-pyrrolidin-1-yl-propyl)-amide (8)

$^1$H NMR (400 MHz, DMSO-d6) δ 8.86 (t, J=5.5 Hz, 1H), 8.44 (d, J=1.8 Hz, 1H), 8.17 (d, J=8.8 Hz, 1H), 8.04 (dd, J=1.8, 8.7 Hz, 1H), 3.40-3.28 (m, 2H), 3.06 (m, 2H), 2.98 (m, 2H), 2.50-2.40 (m, 6H), 1.9 (m, J=3.7 Hz, 4H), 1.78-1.64 (m, 6H).

MS: calcd for C$_{21}$H$_{26}$ClN$_3$O, 371.18. found 372.17 (M+H)$^+$.

9-Chloro-5,6,7,8-tetrahydro-acridine-3-carboxylic acid (3-diethylamino-propyl)-amide (10)

$^1$H NMR (400 MHz, DMSO-d$_6$) δ 8.8 (t, J=5.5 Hz, 1H), 8.44 (d, J=1.8 Hz, 1H), 8.17 (d, J=8.8 Hz, 1H), 8.03 (dd, J=1.7, 8.7 Hz, 1H), 3.38-3.26 (m, 2H), 3.06 (m, 2H), 2.98 (m, 2H), 2.46 (q, J=7.2 Hz, 5H), 1.90 (m, 4H), 1.68 (m, J=7.0 Hz, 2H), 0.95 (t, J=7.1 Hz, 6H).

MS: calcd for C$_{21}$H$_{28}$ClN$_3$O, 373.93. found 374.19 (M+H)$^+$.

Azepan-1-yl-(9-chloro-5,6,7,8-tetrahydro-acridin-3-yl)-methanone (12)

$^1$H NMR (400 MHz, DMSO-d$_6$) δ 8.17 (d, J=8.6 Hz, 1H), 7.85 (d, J=1.7 Hz, 1H), 7.6 (dd, J=1.7, 8.6 Hz, 1H), 3.61 (dd, J=5.6, 6.6 Hz, 2H), 3.35-3.28 (m, 2H), 3.05 (m, 2H), 2.98 (m, 2H), 1.89 (m, 4H), 1.76 (m, J 6.2 Hz, 2H), 1.60 (m, 2H), 1.53 (m, 4H).

MS: calcd for C$_{22}$H$_{23}$ClN$_2$O, 342.15. found 343.17 (M+H)$^+$.

9-Chloro-5,6,7,8-tetrahydro-acridine-3-carboxylic acid [3-(4-propyl-piperazin-1-yl)-propyl]-amide (13)

$^1$H NMR (400 MHz, DMSO-d$_6$) δ 8.84 (t, J=5.5 Hz, 1H), 8.45 (d, J=1.8 Hz, 1H), 8.17 (d, J=8.8 Hz, 1H), 8.04 (dd, J=1.8, 8.7 Hz, 1H), 3.38-3.28 (m, 2H), 3.06 (m, 2H), 2.98 (m, 2H), 2.36 (m, J=7.0 Hz, 9H), 2.19 (t, J=7.7 Hz, 2H), 1.9 (m, J=4.0 Hz, 4H), 1.71 (m, J=7.0 Hz, 2H), 1.4 (m, J=7.41 Hz, 2H), 0.83 (t, J=7.4 Hz, 3H).

MS: calcd for C$_{24}$H$_{33}$ClN4O, 428.23. found 429.20 (M+H)$^+$.

9-Chloro-5,6,7,8-tetrahydro-acridine-3-carboxylic acid [3-(benzyl-methyl-amino)-propyl]-amide (14)

$^1$H NMR (400 MHz, DMSO-d$_6$) δ 8.76 (t, J=5.6 Hz, 1H), 8.44 (d, J=1.8 Hz, 1H), 8.17 (d, J=8.8 Hz, 1H), 8.02 (dd, J=1.7, 8.8 Hz, 1H), 7.33-7.16 (m, 5H), 3.47 (s, 2H), 3.38 (d, J=6.7 Hz, 1H), 3.34 (d, J=6.8 Hz, 1H), 3.33-3.28 (m, 2H), 3.06 (m, 2H), 2.99 (m, 2H), 2.42 (t, J=6.9 Hz, 1H), 2.12 (s, 3H), 1.90 (m, J=3.1 Hz, 1H), 1.77 (m, J=7.0 Hz, 2H).

MS: calcd for C$_{25}$H$_{28}$ClN$_3$O, 421.19. found 422.14 (M+H)$^+$.

9-Chloro-5,6,7,8-tetrahydro-acridine-3-carboxylic acid [3-(4-methyl-piperazin-1-yl)-propyl]-amide (15)

$^1$H NMR (400 MHz, DMSO-d$_6$) δ 8.82 (t, J=5.5 Hz, 1H), 8.45 (d, J=1.8 Hz, 1H), 8.17 (d, J=8.8 Hz, 1H), 8.04 (dd, J=1.7, 8.7 Hz, 1H), 3.38-3.28 (m, 2H), 3.06 (m, 2H), 2.98 (m, 2H), 2.36 (m, J=7.0 Hz, 8.5H), 2.14 (s, 3H), 1.9 (m, J=4.1 Hz, 4H), 1.71 (m, J=7.0 Hz, 2H).

MS: calcd for C$_{22}$H$_{28}$ClN$_4$O, 400.20. found 401.20 (M+H)$^+$.

9-chloro-N-(2-(1-methylpyrrolidin-2-yl)ethyl)-5,6,7,8-tetrahydroacridino-3-carboxamide $^1$H NMR (DMSO-d6, 400 MHz) δ(ppm) 1.50 (m, 2H), 1.62 (m, 2H), 1.90 (m, 4H), 1.95 (m, 2H), 2.05 (m, 2H), 2.22

(s, 3H), 2.95 (m, 3H), 3.03 (m, 2H), 3.34 (m, 2H), 8.00 (dd, J=8.8 Hz, J=1.7 Hz, 1H), 8.13 (d, J=8.8 Hz, 1H), 8.43 (d, J=1.5 Hz, 1H), 8.79 (t, J=5, 5 Hz, 1H).

MS: calcd for $C_{21}H_{26}ClN_3O$, 371.18. found 371.95 $(M+H)^+$.

9-chloro-N-(3-(pyrrolidin-1-ylmethyl)benzyl)-5,6,7,8-tetrahydroacridine-3-carboxamide $^1$H NMR (DMSO-d6, 400 MHz) δ(ppm): 1.71 (m, 4H), 1.85 (m, 4H), 2.50 (m, 2H), 2.97 (m, 2H), 3.05 (m, 2H), 3.37 (m, 2H), 3.66 (m, 2H), 4.54 (d, J=5.7 Hz, 2H), 7.28 (m, 4H), 8.09 (dd, J=8.8 Hz, J=1.6 Hz, 1H), 8.18 (d, J=8.8 Hz, 1H), 8.52 (d, J=1.4 Hz, 1H), 9.36 (t, J=6.0 Hz, 1H).

MS: calcd for $C_{26}H_{28}ClN_3O$, 433.19. found 433.93 $(M+H)^+$.

9-chloro-N-(3-(pyrrolidin-1-ylmethyl)phenyl)-5,6,7,8-tetrahydroacridine-3-carboxamide $^1$H NMR (DMSO-d6, 400 MHz) δ(ppm): 1.71 (m, 4H), 1.91 (m, 4H), 2.54 (m, 2H), 3.00 (m, 2H), 3.09 (m, 2H), 3.35 (m, 2H), 3.61 (s, 2H), 7.07 (d, J=7.5 Hz, 1H), 7.31 (d, J=7.5 Hz, 1H), 7.75 (d, J=8.6 Hz, 1H), 7.84 (s, 1H), 8.15 (dd, J=9.0 Hz, J=1.6 Hz, 1H), 8.23 (d, J=8.6 Hz, 1H), 8.65 (d, J=1.6 Hz, 1H).

MS: calcd for $C_{25}H_{26}ClN_3O$, 419.18. found 419.94 $(M+H)^+$.

9-chloro-N-(3-(2-methylpiperidin-1-yl)propyl)-5,6,7,8-tetrahydroacridine-3-carboxamide RMN $^1$H NMR (DMSO-d6, 400 MHz) δ(ppm): 0.99 (d, J=6.3 Hz, 3H), 1.21 (m, 2H), 1.40 (m, 1H), 1.57 (m, 3H), 1.70 (m, 2H), 1.90 (m, 4H), 2.08 (m, 1H), 2.28 (m, 2H), 2.72 (m, 1H), 2.82 (m, 1H), 2.95 (rn, 2H), 3.05 (m, 2H), 3.30 (m, 2H), 8.03 (dd, J=8.7 Hz, J=1.7 Hz, 1H), 8.15 (d, J=8.8 Hz, 1H), 8.44 (d, J=1.4 Hz, 1H), 8.80 (t, J=5.4 Hz, 1H).

MS: calcd for $C_{22}H_{30}ClN_3O$, 399.21. found 400.00 $(M+H)^+$.

N-(2-(azepan-1-yl)ethyl)-9-chloro-5,6,7,8-tetrahydroacridine-3-carboxamide $^1$H RMN (DMSO-d6, 400 MHz) δ(ppm): 1.60 (m, 4H), 1.75 (m, 4H), 1.90 (m, 4H), 2.97 (m, 2H), 3.06 (m, 2H), 3.14 (m, 6H), 3.75 (m, 2H), 8.06 (dd, J=8.8 Hz, J=1.7 Hz, 1H), 8.18 (d, J=8.8 Hz, 1H), 8.49 (d, J=1.5 Hz, 1H), 8.95 (m, 1H).

MS: calcd for $C_{22}H_{28}ClN_3O$, 385.19. found 385.96 $(M+H)^+$.

9-chloro-N-(2-(piperidin-1-yl)ethyl)-5,6,7,8-tetrahydroacridine-3-carboxamide $^1$H RMN (DMSO-d6, 400 MHz) δ(ppm) 1.37 (m, 2H), 1.48 (m, 4H), 1.88 (m, 4H), 2.39 (m, 4H), 2.49 (m, 2H), 2.95 (m, 2H), 3.04 (m, 2H), 3.43 (m, 2H), 8.03 (dd, J=8.8 Hz, J=1.5 Hz, 1H), 8.14 (d, J=8.8 Hz, 1H), 8.43 (s, 1H), 8.69 (t, J=5.3 Hz, 1H).

MS: calcd for $C_{21}H_{26}ClN_3O$, 371.18. found 371.95 $(M+H)^+$.

(9-chloro-5,6,7,8-tetrahydroacridin-3-yl)(4-((1-methylpiperidin-4-yl)methyl)piperazin-1-yl)methanone $^1$H RMN (DMSO-d6, 400 MHz) δ(ppm): 1.08 (m, 2H), 1.42 (s, 1H), 1.63 (m, 2H), 1.78 (m, 2H), 1.88 (m, 4H), 2.10 (s, 3H), 2.12 (m, 2H), 2.35 (m, 4H), 2.71 (m, 2H), 2.95 (m, 2H), 3.03 (m, 2H), 3.37 (m, 2H), 3.53 (m, 2H), 7.61 (dd. J=8.6 Hz, J=1.5 Hz, 1H), 7.87 (d, J=1.4 Hz, 1H), 8.16 (d, 8.6 Hz, 1H).

MS: calcd for $C_{28}H_{33}ClN_4O$, 440.23. found 441.02 $(M+H)^+$.

(9-chloro-5,6,7,8-tetrahydroacridine-3-yl)(4-(1-methylpiperidin-4-yl)piperazin-1-yl)methanone $^1$H RMN (IDMSO-d6, 400 MHz) δ(ppm): 1.40 (m, 2H), 1.68 (m, 2H), 1.83 (m, 2H), 1.88 (m, 4H), 2.11 (s, 3H), 2.16 (m, 1H), 2.51 (m, 2H), 2.55 (m, 2H), 2.76 (m, 2H), 2.96 (m, 2H), 3.04 (m, 2H), 3.35 (m, 2H), 3.65 (m, 2H), 7.62 (dd, J=8.3 Hz, J=1.2 Hz, 1H), 7.88 (s, 1H), 8.17 (d, J=8, 7 Hz, 1H).

MS: calcd for $C_{24}H_{31}ClN_4O$, 426.22. found 427.01 $(M+H)^+$.

(9-chloro-5,6,7,8-tetrahydroacridin-3-yl)(piperidin-1-yl)methanone $^1$H RMN (DMSO-d6, 400 MHz) δ (pprn): 1.63 (m, 6H), 1.89 (m, 4H), 2.98 (m, 2H), 3.05 (m, 2H), 3.34 (m, 2H), 3.59 (rn, 2H), 7.61 (dd, J=8.6 Hz, J=1.6 Hz, 1H), 7.87 (d, J=1.3 Hz, 1H), 8.18 (d, J=8.6 Hz, 1H).

MS: calcd for $C_{19}H_{21}ClN_2O$, 328.13. found 328.97 $(M+H)^+$.

N-((1-benzylpiperidin-4-yl)methyl)-9-chloro-5,6,7,8-tetrahydroacridine-3-carboxamide $^1$H RMN (DMSO-d6, 400 MHz) δ (pprn): 1.21 (m, 2H), 1.61 (m, 1H), 1.68 (m, 2H), 1.90 (m, 6H), 2.80 (m, 2H), 2.98 (m, 2H), 3.05 (m, 2H), 3.19 (rn, 2H), 3.52 (s, 2H), 7.24 (m, 1H), 7.31 (m, 4H), 8.04 (dd, J=8.6 Hz, J=1.4 Hz, 1H), 8.17 (d, J=8.6 Hz, 1H), 8.46 (d, J=1.4 Hz, 1H), 8.78 (t, J=5.4 Hz, 1H).

MS: calcd for $C_{27}H_{30}ClN_3O$, 447.21. found 447.98 $(M+H)^+$.

9-chloro-N-((1-(3-phenylpropyl)piperidin-4-yl)methyl)-5,6,7,8-tetrahydroacridine-3-carboxamide $^1$H RMN (DMSO-d6, 400 MHz) δ (ppm): 1.21 (m, 3H), 1.50 (m, 1H), 1.70 (m, 4H), 1.90 (m, 6H), 2.27 (m, 1H), 2.55 (m, 2H), 2.89 (m, 2H), 2.98 (m, 2H), 3.06 (m, 2H), 3.21 (m, 2H), 7.17 (m, 3H), 7.27 (m, 2H), 8.04 (dd, J=8.6 Hz, J=1.6 Hz, 1H), 8.16 (d, J=8.6 Hz, 1H), 8.47 (d, J=1.4 Hz, 1H), 8.77 (t, J=5.7 Hz, 1H).

MS: calcd for $C_{29}H_{34}ClN_3O$, 475.24. found 476.01 $(M+H)^+$.

9-chloro-N-((1-phenethylpiperidin-4-yl)methyl)-5,6,7,8-tetrahydroacridine-3-carboxamide $^1$H RMN (DMSO-d6, 400 MHz) δ (ppm): 1.18 (m, 2H), 1.60 (m, 1H), 1.72 (m, 2H), 1.93 (m, 6H), 2.53 (m, 2H) 2.73 (m, 2H), 2.97 (m, 4H), 3.06 (m, 2H), 3.22 (m, 2H), 7.20 (m, 5H), 8.05 (d, J=8.3 Hz, 1H), 8.17 (d, J=8.3 Hz, 1H), 8.48 (s, 1H), 8.78 (t, J=5.5 Hz, 1H).

MS: calcd for $C_{28}H_{32}ClN_3O$, 461.22. found 462.01 $(M+H)^+$.

9-chloro-N-(5-(diethylamino)pentan-2-yl)-5,6,7,8-tetrahydroacridine-3-carboxamide $^1$H RMN (DMSO-d6, 400 MHz) δ (ppm): 0.97 (t, J=7.1 Hz, 6H), 1.20 (m, 4H), 1.52 (m, 5H), 1.90 (m, 4H), 2.53 (m, 4H), 2.98 (m, 2H), 3.04 (m, 2H), 4.10 (m, 1H), 8.05 (dd, J=8.4 Hz, J=1.4 Hz, 1H), 8.16 (d, J=8.8 Hz, 1H), 8.48 (d, J=1.3 Hz, 1H), 8.50 (d, J=8.1 Hz, 1H).

MS: calcd for $C_{23}H_{32}ClN_3O$, 401.22. found 401.96 (M+H)$^+$.

(R)-9-chloro-N-((1-ethylpyrrolidin-2-yl)methyl)-5,6,7,8-tetrahydroacridine-3-carboxamide $^1$H RMN (DMSO-d6, 400 MHz) δ (ppm): 1.11 (t, J=7.1 Hz, 3H), 1.74 (m, 3H), 1.90 (m, 4H) 2.83 (m, 1H), 2.50 (m, 1H), 2.85 (m, 1H), 2.99 (m, 3H), 3.07 (m, 2H), 3.18 (m, 1H) 3.25 (m, 1H), 3.55 (m, 2H), 8.06 (dd, J=8.7 Hz, J=1.7 Hz, 1H), 8.18 (d, J=8.7 Hz, 1H), 8.48 (d, J=1.5 Hz, 1H), 8.80 (t, J=5.2 Hz, 1H).
MS: calcd for $C_{21}H_{26}ClN_3O$, 371.18. found 371.92 (M+H)$^+$.

(S)-9-chloro-N-((1-ethylpyrrolidin-2-yl)methyl)-5,6,7,8-tetrahydroacridine-3-carboxamide $^1$H RMN (DMSO-d6, 400 MHz) δ (ppm): 1.11 (t, J=7.1 Hz, 3H), 1.74 (m, 3H), 1.90 (m, 4H) 2.83 (m, 1H), 2.50 (m, 1H), 2.85 (m, 1H), 2.99 (m, 3H), 3.07 (m, 2H), 3.18 (m, 1H), 3.25 (m, 1H), 3.55 (m, 2H), 8.06 (dd, J=8.8 Hz, J=1.8 Hz, 1H), 8.18 (d, J=8.8 Hz, 1H), 8.48 (d, J=1.5 Hz, 1H), 8.80 (m, 1H).
MS: calcd for $C_{21}H_{26}ClN_3O$, 371.18. found 371.92 (M+H)$^+$.

9-chloro-N-(3-(dimethylamino)-2,2-dimethylpropyl)-5,6,7,8-tetrahydroacridine-3-carboxamide $^1$H RMN (DMSO-d6, 400 MHz) δ (ppm): 0.94 (s, 6H), 1.89 (m, 4H), 2.29 (m, 2H), 2.34 (s, 6H), 2.96 (m, 2H), 3.05 (m, 2H), 3.26 (d, J=5.9 Hz, 2H), 8.01 (dd, J=8.7 Hz, J=1.8 Hz, 1H), 8.16 (d, J=8.7 Hz, 1H), 8.43 (d, J=1.5 Hz, 1H), 8.77 (t, J=5.9 Hz, 1H).
MS: calcd for $C_{21}H_{28}ClN_3O$, 373.19. found 373.92 (M+H)$^+$.

9-chloro-N-(3-(3,4-dihydroisoquinolin-2(1H)-yl)propyl)-5,6,7,8-tetrahydroacridine-3-carboxamide $^1$H RMN (DMSO-d6, 400 MHz) δ (ppm): 1.84 (m, 6H), 2.55 (m, 2H), 2.67 (m, 2H), 2.80 (m, 2H), 2.96 (m, 2H), 3.05 (m, 2H), 3.39 (m, 2H), 3.57 (s, 2H), 7.09 (m, 4H), 7.99 (dd, J=8.8 Hz, J=1.7 Hz, 1H), 8.09 (d, J=8.8 Hz, 1H), 8.44 (d, J=1.5 Hz, 1H), 8.86 (t, J=5.4 Hz, 1H).
MS: calcd for $C_{26}H_{28}ClN_3O$, 433.19. found 433.94 (M+H)$^+$.

The following compounds were also synthesized by using the method mentioned above:

9-chloro-N-(4-(pyrrolidin-1-ylmethyl)benzyl)-5,6,7,8-tetrahydroacridine-3-carboxamide

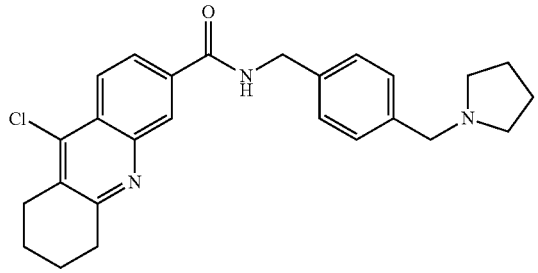 [SMILES: O=C(NCc1ccc(CN2CCCC2)cc1)c1ccc2c(Cl)c3c(nc2c1)CCCC3]

MS: calcd for $C_{26}H_{28}ClN_3O$, 433.19. found 433.91 (M+H)$^+$.

9-chloro-N-((1-(4-methoxybenzyl)piperidin-4-yl)methyl)-5,6,7,8-tetrahydroacridine-3-carboxamide

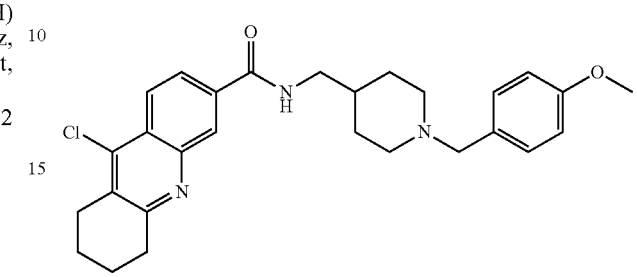

MS: calcd for $C_{28}H_{32}ClN_3O_2$, 477.22. found 477.99 (M+H)$^+$.

9-chloro-N-((1-4-N,N-dimethylbenzyl)piperidin-4-yl)methyl)-5,6,7,8-tetrahydroacridine-3-carboxamide

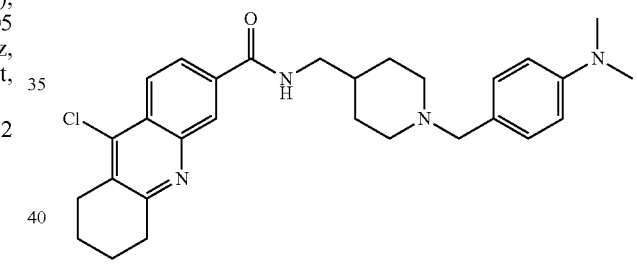

MS: calcd for $C_{29}H_{35}ClN_4O$, 490.25. found 491.00 (M+H)$^+$.

9-chloro-N-((piperidin-4-yl)methyl)-5,6,7,8-tetrahydroacridine-3-carboxamide

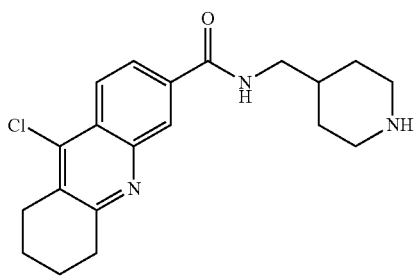 [SMILES: O=C(NCC1CCNCC1)c1ccc2c(Cl)c3c(nc2c1)CCCC3]

MS: calcd for $C_{20}H_{24}ClN_3O$, 357.16. found 357.93 (M+H)$^+$.

9-chloro-N-(3-hydroxy-3-phenyl-2-pyrrolidin-1-ylmethylpropyl)-5,6,7,8-tetrahydroacridine-3-carboxamide

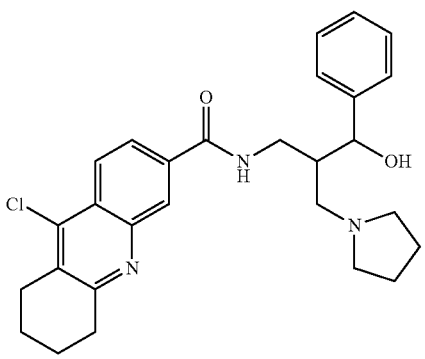 [SMILES: O=C(NCC(CN1CCCC1)C(O)c1ccccc1)c1ccc2c(Cl)c3c(nc2c1)CCCC3]

MS: calcd for $C_{28}H_{32}ClN_3O_2$, 477.22. found 477.99 $(M+H)^+$.

Chlorhydrate of 9-chloro-5,6,7,8-tetrahydroacridine-3-carboxylic acid (2-diethylamino-ethyl)amide

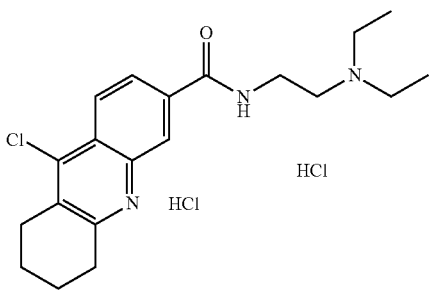 [SMILES: CCN(CC)CCNC(=O)c1ccc2c(Cl)c3c(nc2c1)CCCC3 ; Cl ; Cl]

MS: calcd for $C_{22}H_{26}ClN_2O \cdot 2HCl$, 359.18. found 360.01 $(M+H)^+$.

Other intermediates compounds of formula (VII) were synthesized to give the compounds of formula (I) by a peptic coupling:

Preparation of the Intermediate of Formula (VIIb)

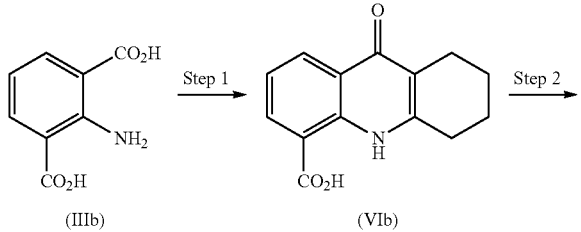

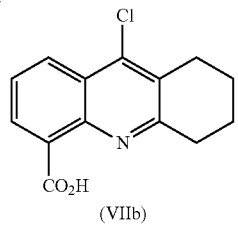

(VIIb)

Step 1: Condensation 9-oxo-5-6,7,8,9,10-hexahydro-acridine-2-carboxylic acid (VIb)

To a suspension of amino acid in diphenyl ether (3 mL), cyclohexanone was added and the reaction mixture was heated to 250° C. for 10 min. Reaction completion was monitored by LC/MS which showed the desired product, the intermediate hydrate but still starting material. Cyclohexanone (0.63 mL) was added and the reaction mixture was heated to 250° C. for another 10 min (monitored by LC/MS, still starting material). The above process was repeated till LC/MS showed complete product formation (5× overall). Excess of cyclohexanone led to lower boiling point of the reaction mixture because cyclohexanone boiling point=155° C. At the end, excess of cyclohexanone was removed under vacuum (rota) and the residue was heated at 250° C. for another 10 min (this permits to reach higher temperature In the reaction mixture, mixture temperature was controlled), LCMS showed the desired product, the reaction mixture was cooled to 25° C.; product was filtered, washed with pentane and dried under vacuum to get 549 mg as a brown solid (Mass excess could be diphenyl ether as 1HNMR showed too much aromatic protons). The crude product was used without further purification.

$^1$H NMR (DMSO-d6, 300 MHz) δ=1.90-2.00 (m, 4H), 2.98-3.07 (m, 2H), 3.13-3.22 (m, 2H), 7.87 (dd, 1H, J=7.5 Hz and J=9.0 Hz), 8.47 (dd, 1H, J=1.5 Hz and J=9.0 Hz), 8.57 (dd, 1H, J=1.5 Hz and J=7.5 Hz)

$^{13}$C NMR (DMSO-d6, 75 MHz) δ=21.2 and 21.4 (2C), 26.8 (1C), 32.8 (1C), 123.5 and 124.7 (2C), 127.4-134.1 (4C), 142.7 and 142.9 (2C), 159.8 (1C), 165.9 (1C)

Step 2: Halogenation 9-chloro-5,6,7,8-tetrahydroacridine-2-carboxylic acid (VIIb)

A suspension of crude carboxylic acid in POCl$_3$ was heated for 1 h at 100° C. The reaction was followed with LCMS which showed no more starting material but the desired product. POCl$_3$ excess was removed under vacuum and the residue was poured in ice, the aqueous residue obtained was triturated, pH was adjusted to 4 with solid NaHCO$_3$, and the solid obtained was filtered to give 127 mg of product alter drying under vacuum. The desired product was purified by reverse flash column chromatography (using Biotage flash+, MeCN/H$_2$O 40/60). 90 mg of the pure desired product was obtained as a beige solid (28%).

$^1$H NMR (DMSO-d6, 300 MHz) δ=1.90-2.00 (m, 4H), 2.98-3.07 (m, 2H), 3.13-3.22 (m, 2H), 7.87 (dd, 1H, J=7.5 Hz and J=9.0 Hz), 8.47 (dd, 1H, J=1.5 Hz and J=9.0 Hz), 8.57 (dd, 1H, J=1.5 Hz and J=7.5 Hz)

$^{13}$C NMR (DMSO-d6. 75 MHz) δ=21.2 and 21.4 (2C), 26.8 (1C), 32.8 (1C), 123.5 and 124.7 (2C), 127.4-134.1 (4C), 142.7 and 142.9 (2C), 159.8 (1C), 165.9 (1C)

Preparation of the Intermediate of Formula (VIIc)

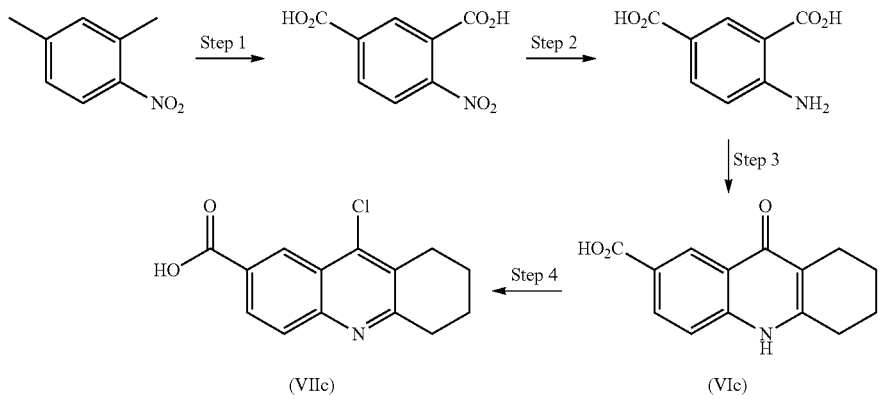

Step 1: Oxidation 4-nitroisophthalic acid

Potassium permanganate was dissolved in water (400 mL) in a flask fitted with a thermometer and a rellux condenser. 4-Nitro-m-xylene was added. The mixture was cautiously heated to 85° C.

Cooling to maintain the reaction mixture at 85° C. was necessary (the hot bath was removed and put back). After 20 min, the mixture was gently refluxed for 3 h (the purple colour had disappeared and the mixture was almost black). The warm mixture was filtered through celite. The cold filtrate was acidified with concentrated sulphuric acid and a milky suspension was obtained. Extraction with EtOAc (3×0.5 L). The combined organic layers were dried (Na$_2$SO$_4$) and concentrated to give a white solid; purification by flash chromatography using EtOAc/heptane/AcOH 10:10:1 as eluent gave 2 fractions of white solid (42% global yield).

Step 2: Nitro Reduction 4-aminoisophthalic acid

A solution of nitro-isophtalic acid in EtOH (absolu, 40 mL) was injected in the H-cube (50° C., Pd/C 10%, Full H2, 1 mL/min).

The resulting solution was controlled with LCMS which showed full conversion toward the desired product.

In order to avoid nitroso side product traces, the resulting was injected a second time in the H-Cube using the method described above. EtOH was removed under vacuum and 0.83 g al the pure desired aniline was obtained as a white solid (97% yield). The clean aniline was used without further purification in condensation step.

Step 3: Condensation 9-oxo-5,6,7,8,9,10-hexahydro-acridine-4-carboxylic acid (VIc)

To a suspension of 2-amino isophtalic acid in diphenyl ether (8 mL) was added cyclohexanone (1.5 mL) and the reaction mixture was heated to 250° C. for 10 min. Reaction completion was monitored by LCMS. Cyclohexanone was added and the reaction mixture was heated to 250° C. for another 10 min. The above process was repeated till LCMS showed complete product formation. But after 6 cycles LCMS showed no more progression so cyclohexanone was completely removed under vacuum. Excess of cyclohexanone led to lower boiling point of the reaction mixture because cyclohexanone boiling point=155° C. Excess of cyclohexanone was removed under vacuum (rota), then, 1.5 mL of cyclohexanone was added to the residue and the reaction mixture was heated to 250° C. for 10 min (this permits to reach higher temperature in the reaction mixture). LCMS showed complete conversion toward the desired product.

The reaction mixture was cooled to 25° C., product was filtered, washed with pentane and then with MeOH, dried under vacuum to get the pure desired product as a beige solid (700 mg, 63%).

Step 4: Halogenation 9-chloro-5,6,7,8-tetrahydroacridine-4-carboxylic acid (VIIc)

A suspension of crude carboxylic acid in POCl$_3$ was heated for 1 h at 100° C. The reaction was followed with LCMS which showed complete conversion toward the desired product. The reaction was cooled to rt and POCl$_3$ excess was removed under vacuum. The residue was poured in ice and pH was adjusted to 4 with solid NaHCO$_3$. The aqueous mixture was triturated and let overnight at 5° C. (fridge). The solid obtained was filtered and washed with water to get a dark grey powder. Rapid fash chromatography (AcOEt/MeOH 95/5) afforded 76 mg of the pure desired product (beige solid, 44% yield). 1H NMR showed traces or EtOAc, so the product was dried overnight under high vacuum and ½ h at 120° C. at ambient pressure.

$^1$H NMR (DMSO-d6. 300 MHz) δ=1.85-1.95 (m, 4H), 2.93-3.02 (m, 2H), 3.03-3.10 (m, 2H), 8.01 (d, 1H, J=9.0 Hz), 8.20 (dd, 1H, J=2.0 Hz and J=9.0 Hz), 8.75 (d, 1H, J=2.0 Hz), 13.35 (br s, 1H)

¹³C NMR (DMSO-d6, 75 MHz) δ=22.2 (2C), 27.4 (1C), 34.1 (1C), 124.2 (1C), 126.1 (1C), 129.2-130.2 (4C), 141.4 (1C), 148.1 (1C), 162.5 (1C), 167.1 (1C)

Preparation of the Intermediate of Formula (VIIf)

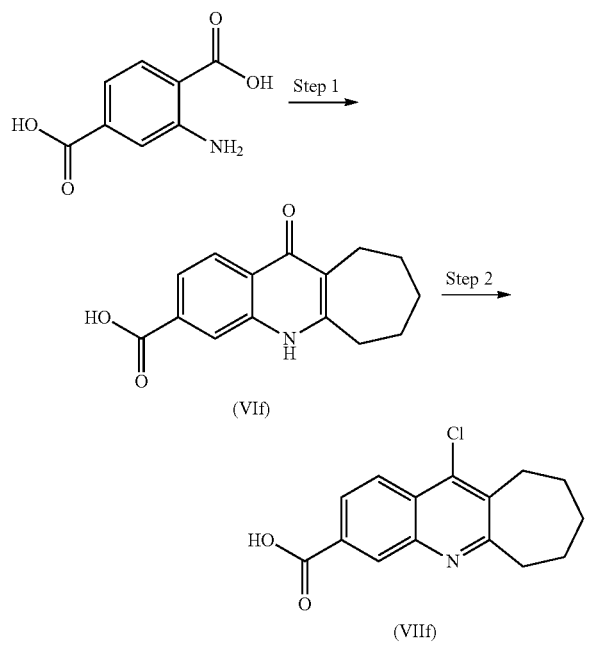

(20 Vol) and stirred for 20 min. The precipitated solid was filtered, washed with hexane (20 Vol) and dried under vacuum. The crude product (1.39 g) was taken as such for next step.

¹H NMR (300 MHz, DMSO): δ=13.28 (bs, 1H), 11.61 (bs, 1H), 8.14-8.16 (d, 2H, J=8.1 Hz), 7.73-7.757 (m, 1H), 2.77-2.84 (m, 4H), 1.69-1.81 (m, 4H), 1.46 (m, 2H).

Step 2: Halogenation 11-chloro-7,8,9,10-tetrahydro-6H-cyclohepta[b]quinoline-3-carboxylic acid Compound VIf (200 mg, 0.0007mols) was taken in phosphorus oxychloride (10 Vol) and refluxed at 95° C. for 8 hrs. Reaction was monitored by TLC. After completion, the reaction mixture was cooled to 25° C. and quenched the reaction mass with crushed ice and basified to a pH 4 to 5 using 10% NaHCO₃ solution. The aqueous layer was extracted with ethyl acetate (10 Vol×3). Combined organic layer was dried over sodium sulphate and concentrated to get yellow solid (180 mg, 86%).

¹H NMR (300 MHz, DMSO): δ=8.456-8.460 (d, 1H, J=1.2 Hz), 8.18-8.21 (d, 1H, J=8.7 Hz), 8.104-8.138 (d, 1H. 8.7 Hz), 3.20-3.25 (m, 4H), 1.85-1.86 (m, 2H), 1.70-1.73 (m, 4H).

Preparation of the Intermediates of Formula (VIIh, VIIi, VIIj)

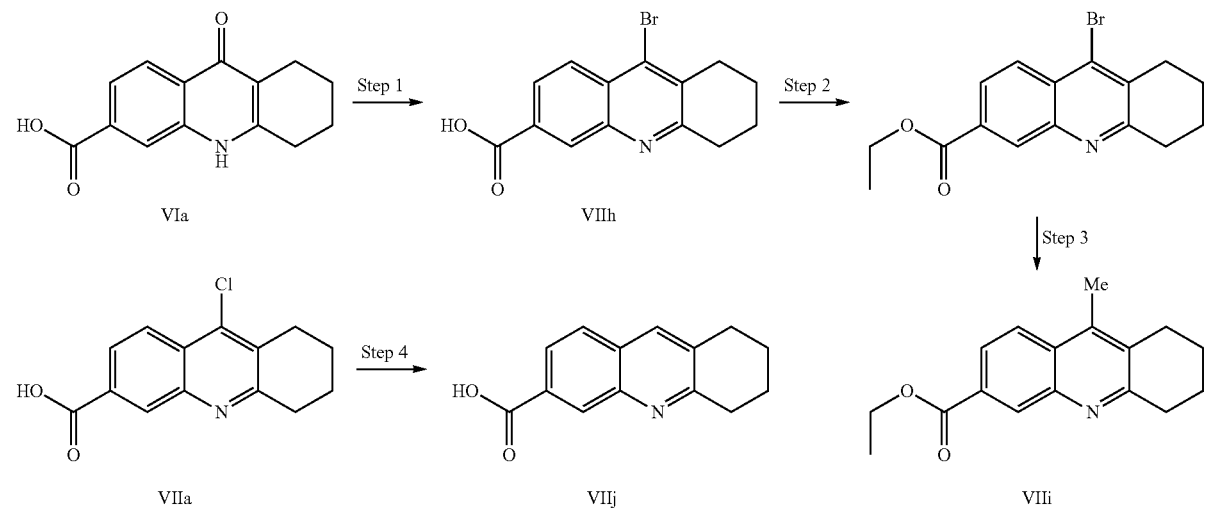

Step 1: Condensation 11-oxo-6,7,8,9,10111-hexahydro-5H-cyclohepta[b]quinoline-3-carboxylic acid (VIf)

To a suspension al 2-Amincterephthalic acid (1 g, 0.005 mols) in diphenyl ether (15 mL) added cycloheptanone (40 mL) at 25° C. and the reaction mixture was heated to 250° C. for 15 min. LC/MS showed 95% product formation. The reaction mixture was cooled to 23-25° C. and added hexane Step 1: Halogenation 9-bromo-5,6,7,8-tetrahydroacridine-3-carboxylic acid A suspension of 9-oxo-5,6,7,8,9,10-hexahydro-acridine-3-carboxylic acid (1 g, 0.42mmols) in toluene (10 mL) was heated with phosphorous oxybromide (3.54 g, 1.2mmols) to 100° C. for 4 h. Reaction completion was monitored by TLC. After completion, the reaction mixture was cooled to 25° C., quenched with solid ice (50 g) and the pH was adjusted to 4-5 with solid sodium bicarbonate. The precipitated solid was filtered, washed with water (250 mL) and dried under vacuum to gel the crude product as off white solid. The crude product was purified by preparative HPLC to get pure bromo compound (65 mg. 5%) as off white solid.

$^1$H NMR (300 MHz, DMSO): δ=8.44 (s, 1H), 8.19-8.16 (d, 1H, J=9 Hz), 8.08-8.11 (d, 1H, J=9 Hz), 3.07 (m, 2H), 2.97 (m, 2H), 1.89 (m, 4H).

Step 2: Esterification

Ethyl 9-bromo-5,6,7,8-tetrahydroacridine-3-carboxylate

A suspension of 9-oxo-5,6,7,8,9,10-hexahydro-acridine-3-carboxylic acid (1 g, 0.42 mmols) in toluene (10 mL) was heated with phosphorous oxybromide (3.54 g, 1.2 mmols) to 100° C. for 4 h. Reaction completion was monitored by TLC. Alter completion, the reaction mixture was cooled to 25° C., quenched with methanol (10 mL), concentrated the reaction mixture under vacuum and purified the crude product with silica gel column (60:120). Product eluted with 2% methanol in chloroform. Fractions were collected and concentrated to get the pure product as off white solid. This compound was taken as such to next step.

$^1$H NMR (300 MHz, DMSO): δ=8.47-8.49 (m, 1H), 8.21-8.27 (t, 1H, J=7.5 Hz), 8.09-8.13 (m, 1H), 3.95 (s, 3H), 3.08 (m, 2H), 2.99 (m, 2H), 1.91 (m. 4H).

Step 4: Methylation

Ethyl 9-methyl-5,6,7,8-tetrahydroacridine-3-carboxylate

To a solution of 9-Bromo-5,6,7,8-tetrahydro-acridlne-3-carboxylic acid methyl ester (1 g, 0.42 mmols) in DME (15 mL) and THF (10 mL), added potassium carbonate (450 mg, 0.32 mmols), methyl boronic acid (150 mg, 0.23mmols) and the reaction mixture was degassed with argon. Added tetrakis (triphenyl phosphine) palladium (0) (130 mg, 0.016mmols) and the reaction mixture was heated at 90° C. for 8 h. Reaction completion was monitored by TLC. After completion, the reaction mixture was cooled to 25° C., diluted with ethyl acetate and filtered through celite. Filtrate was concentrated and purified by silica gel (60:120) column. Product eluted with 10% ethyl acetate in ether. Fractions were collected and concentrated to get the product as off while solid with 70% purity. The product was further purified by preparative HPLC.

$^1$H NMR (300 MHz, CDCl3): δ=8.73 (s, 1H), 8.00-8.08 (m, 2H), 3.99 (s, 3H), 3.01-3.18 (m, 2H), 2.93 (m, 2H), 2.59 (s, 3H), 1.90-2.03 (m, 4H).

Step 4: Saponification 9-methyl-5,6,7,8-tetrahydroacridine-3-carboxylic acid

A solution 9-methyl-5,6,7,8-tetrahydro-acridine-3-carboxylic acid methyl ester (120 mg, 0.04mmols) in THF:water (6 mL:4 mL) added solid sodium hydroxide (75 mg, 0.16mmols) and heated the reaction mixture at 70° C. for 3 h. Reaction completion was monitored by TLC. After completion, the reaction mixture was diluted with water and washed with ethyl acetate. The aqueous layer was acidified to pH 3-4 using 1.5N hydrochloric acid solution. Precipitated product was filtered and dried to get the pure product as off white solid (25 mg, 22%). Compound was purified by preparative HPLC.

$^1$H NMR (300 MHz. DMSO, TFA): δ=8.69 (s, 1H), 8.57-8.60 (d, 1H, J=9 Hz), 8.26-8.29 (d, 1H, J=9 Hz), 3.32 (m, 2H), 3.01 (m, 2H), 2.85 (s, 3H), 1.94 (m, 4H).

Step 4: Hydrogenation 5,6,7,8-tetrahydroacridine-3-carboxylic acid

To a solution of 9-Chloro-5,8,7,8-tetrahydro-acridine-3-carboxylic acid (1 g, 0.2mmols) in ethanol (10 mL), added 50% wet palladium on carbon 10% (200 mg) and the reaction mixture was hydrogenated at 3 kg for 12 h. Reaction completion was monitored by TLC. The reaction mixture was filtered through celite, washed with ethanol and concentrated under vacuum to get the crude product. (51% by LC/MS). Purification by silica gel (60:120) chromatography with 5% methanol in chloroform and afforded 80 mg (15%) of pure product.

$^1$H NMR (300 MHz. DMSO): δ=13.15 (s, 1H), 8.43 (s, 1H), 8.09 (s, 1H), 7.91-7.98 (t, 1H, J=9.6 Hz), 2.965-3.072 (m, 4H), 1.878-1.972 (m, 4H).

| Examples | Names |
|---|---|
| 1 | 9-Chloro-5,6,7,8-tetrahydro-acridine-3-carboxylic acid [1-(3-methyl-benzyl)-piperidin-4-ylmethyl]-amide |
| 2 | 9-Chloro-5,6,7,8-tetrahydro-acridine-3-carboxylic acid (1-ethyl-pyrrolidin-2-ylmethyl)-amide |
| 3 | 9-Chloro-5,6,7,8-tetrahydro-acridine-3-carboxylic acid (2-dipropylamino-ethyl)-amide |
| 4 | 9-Chloro-5,6,7,8-tetrahydro-acridine-3-carboxylic acid [2-(butyl-ethyl-amino)-ethyl]-amide |
| 5 | 9-Chloro-5,6,7,8-tetrahydro-acridine-3-carboxylic acid [3-(benzyl-ethyl-amino)-propyl]-amide |
| 6 | 9-Chloro-5,6,7,8-tetrahydro-acridine-3-carboxylic acid (3-dipropylamino-propyl)-amide |
| 7 | 9-Chloro-5,6,7,8-tetrahydro-acridine-3-carboxylic acid (2-diethylamino-ethyl)-amide |
| 8 | 9-Chloro-5,6,7,8-tetrahydro-acridine-3-carboxylic acid (3-pyrrolidin-1-yl-propyl)-amide |
| 9 | 9-Chloro-5,6,7,8-tetrahydro-acridine-3-carboxylic acid [3-(2,6-dimethyl-piperidin-1-yl)-propyl]-amide |
| 10 | 9-Chloro-5,6,7,8-tetrahydro-acridine-3-carboxylic acid (3-diethylamino-propyl)-amide |
| 11 | 9-Chloro-5,6,7,8-tetrahydro-acridine-3-carboxylic acid (2-dimethylamino-ethyl)-amide |
| 12 | Azepan-1-yl-(9-chloro-5,6,7,8-tetrahydro-acridin-3-yl)-methanone |
| 13 | 9-Chloro-5,6,7,8-tetrahydro-acridine-3-carboxylic acid [3-(4-propyl-piperazin-1-yl)-propyl]-amide |
| 14 | 9-Chloro-5,6,7,8-tetrahydro-acridine-3-carboxylic acid [3-(benzyl-methyl-amino)-propyl]-amide |
| 15 | 9-Chloro-5,6,7,8-tetrahydro-acridine-3-carboxylic acid [3-(4-methyl-piperazin-1-yl)-propyl]-amide |
| 16 | [1,4']Bipiperidinyl-1'-yl-(9-chloro-5,6,7,8-tetrahydro-acridin-3-yl)-methanone |
| 17 | 9-chloro-N-(2-(1-methylpyrrolidin-2-yl)ethyl)-5,6,7,8-tetrahydroacridino-3-carboxamide |
| 18 | 9-chloro-N-(3-(pyrrolidin-1-ylmethyl)benzyl)-5,6,7,8-tetrahydroacridine-3-carboxamide |
| 19 | 9-chloro-N-(3-(pyrrolidin-1-ylmethyl)phenyl)-5.6,7,8-tetrahydroacridine-3-carboxamide |
| 20 | 9-chloro-N-(3-(2-methylpiperidin-1-yl)propyl)-516,7,8-tetrahydroacridine-3-carboxamide |
| 21 | 9-chloro-N-(4-(pyrrolidin-1-ylmethyl)benzyl)-5,6,7,8-tetrahydroacridine-3-carboxamide |
| 22 | 9-chloro-N-((1-(4-methoxybenzyl)piperidin-4-yl)methyl)-5,6,7,8-tetrahydroacridine-3-carboxamide |
| 23 | 9-chloro-N-((1-4-N,N-dimethylbenzyl)piperidin-4-yl)methyl)-5,6,7,8-tetrahydroacridine-3-carboxamide |
| 24 | 9-chloro-N-((piperidin-4-yl)methyl)- 5,6,7,8-tetrahydroacridine-3-carboxamide |
| 25 | 9-chloro-N-(3-hydroxy-3-phenyl-2-pyrrolidin-1-ylmethylpropyl)- 5,6,7,8-tetrahydroacridine-3-carboxamide |

| Examples | Names |
|---|---|
| 26 | chlorhydrate of 9-chloro-5,6,7,8-tetrahydro-acridine-3-carboxylic acid (2-diethylamino-ethyl)-amide |
| 27 | N-(2-(azepan-1-yl)ethyl)-9-chloro-5,6,7,8-tetrahydroacridine-3-carboxamide |
| 28 | 9-chloro-N-(2-(piperidin-1-yl)ethyl)-5,6,7,8-tetrahydroacridine-3-carboxamide |
| 29 | (9-chloro-5,6,7,8-tetrahydroacridine-3-yl)(4-((1-methylpiperidin-4-yl)methyl)piperazin-1-yl)methanone |
| 30 | (9-chloro-5,6,7,8-tetrahydroacridine-3-yl)(4-(1-methylpiperidin-4-yl)piperazin-1-yl)methanone |
| 31 | (9-chloro-5,6,7,8-tetrahydroacridine-3-yl)(piperidin-1-yl)methanone |
| 32 | N-((1-benzylpiperidin-4-yl)methyl)-9--chloro-5,6,7,8-tetrahydroacridine-3-carboxamide |
| 33 | 9-chloro-N-((1-(3-phenylpropyl)piperidin-4-yl)methyl)-5,6,7,8-tetrahydroacridine-3-carboxamide |
| 34 | 9-chloro-N-((1-phenethylpiperidin-4-yl)methyl)-5,6,7,8-tetrahydroacridine-3-carboxamide |
| 35 | 9-chloro-N-(5-(diethylamino)pentan-2-yl)-5,6,7,8-tetrahydroacridine-3-carboxamide |
| 36 | (R)-9-chloro-N-((1-ethylpyrrolidin-2-yl)methyl)-5,6,7,8-tetrahydroacridine-3-carboxamide |
| 37 | (S)-9-chloro-N-((1-ethylpyrrolidin-2-yl)methyl)-5,6,7,8-tetrahydroacridine-3-carboxamide |
| 38 | 9-chloro-N-(3-(dimethylamino)-2,2-dimethylpropyl)-5,6,7,8-tetrahydroacridine-3-carboxamide |
| 39 | 9-chloro-N-(3-(3,4-dihydroisoquinolin-2(1H)-yl)propyl)-5,6,7,8-tetrahydroacridine-3- carboxamide |

Representative Cysteine Proteases

USP7 Protein Production & Purification

The cDNA encoding USP7 was obtained by PCR amplification from placenta mRNA. USP7 cDNA was subcloned by PCR into a baculovirus expression vector (pFastBac-HT; Invitrogen). Full-length wild-type human USP7 and its catalytic mutant (cysteine 223 replaced by alanine, C223A) were produced as N-terminally His-tagged fusions in *Spodoptera frugiperda* cells (Sf9, Invitrogen), using the Bac-to-Bac Baculovirus system from Invitrogen according to the manufacturer's instructions. pFastBac-HT-B-USP7 was used to transform DH10bac cells (Invitrogen), and blue/white selection was carried out on X-gal/IPTG agar plates. Bacmid DNA was prepared by an alkaline lysis procedure. The integrity of the bacmid minipreps and their orientation were checked by PCR, using generic and specific primers. Sf9 insect cells were cultured in InsectXpress medium (Cambrex) at 27° C. and transfected with the corresponding bacmid, using GeneShuttle 40 (Q-BIOgen). Viruses were recovered in the supernatant 72 h after transfection. Viruses were amplified by infecting insect cells (Sf9 or High Five cells; invitrogen) in 50 ml InsectXpress medium in a 150 cm² cell culture flask with 500 µl of the supernatant from transfected Sf9 cells. Following the second round of amplification, infected cells were recovered by rapid SDS lysis, boiled for 5 min at 100° C., sonicated briefly and centrifuged for 20 min at 14,000 g. Expression levels in infected Sf9 cells were compared with those in uninfected cells. Fusion proteins were then allowed to bind to TALON beads (BD Biosciences, TALON metal affinity resin) for 30 min at 4° C. with gentle rocking. Beads were extensively washed (50 mM sodium phosphate buffer pH 7.0, 500 mM NaCl, 10 mM Imidazole, 0.5% Triton X-100 and 10% glycerol) and bound proteins were eluted in wash buffer supplemented with 250 mM Imidazole (Sigma). Eluted fractions were resolved on 4-12% NuPAGE gels (Novex, Invitrogen). Fractions containing high concentrations of purified proteins (purity >95%) were dialyzed (20 mM Tris HCl pH 7.6, 200 mM NaCl, 1 mM DTT, 1 mM EDTA and 10% glycerol) were aliquoted and snap frozen in liquid nitrogen before storage at −80° C.

USP7 Activity Assay

USP7 was diluted in USP buffer (50 mM Tris HCl; 0.5 mM EDTA; 5 mM DTT; 0.01% Triton X-100; Bovine Serum Albumin 0.05 mg·ml$^{-1}$ pH7.6). Compounds stocks (10 mM) were stored at −20° C. in DMSO. Compounds were tested at different concentrations: from 200 µM to 91 nM.

Reactions were performed as duplicates in Black 384 well plates (small volumes microplates; Greiner; 10 µl final reaction volume). The substrate concentration for USP7 was 300 nM Ub-AMC (*Chem. Biol.*, 2003, 10, p. 837-846) (Boston Biochem). The concentrations of the enzyme (USP7) in specificity assays was 100 pM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/− compounds) diluted in assay buffer. Reactions were incubated for 60 minutes at 37° C. Reactions were stopped by adding acetic acid (100 mM final). Readings were performed on a Pherastar Fluorescent Reader (BMG). λ Emission 380 nm; λ Excitation=460 nm. Data (mean values +/− standard deviation) were analyzed as % of control (no compound) and plotted as percentage versus the Log of the compound concentration using GraphPad (Prism). Data were fitted to a sigmoidal model (variable slope).

USP5 Activity Assay

USP5 was diluted in USP buffer (50 mM Tris HCl; 0.5 mM EDTA; 5 mM DTT; 0.01% Triton X-100; Bovine Serum Albumin 0.05 mg·ml$^{-1}$ pH 7.6). Compounds stocks (100 mM) were stored at −20° C. in DMSO. Compounds were tested at different concentrations: from 200 µM to 91 nM.

Reactions were performed as duplicates in Black 384 well plates (small volume microplates; Greiner; 10 µl final reaction volume). The substrate concentration for USP5 was 300 nM Ub-AMC (Boston Biochem). The concentrations of the enzyme (USP5) in specificity assays was 300 pM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/− compounds) diluted in assay buffer. Reactions were incubated for 60 minutes at 37° C. Reactions were stopped by adding acetic acid (100 mM final). Readings were performed on a Pherastar Fluorescent Reader (BMG). λ Emission 380 nm; λ Excitation=460 nm. Data (mean values +/− standard deviation) were analyzed as % of control (no compound) and plotted as percentage versus the Log of the compound concentration using GraphPad (Prism). Data were fitted to a sigmoidal model (variable slope).

Cloning & Purification of USP8

The cDNA encoding USP8 was obtained by PCR amplification from placenta mRNA. USP8 cDNA was subcloned by PCR into a baculovirus expression vector (pFastBac-HT; Invitrogen). A cDNA encoding a mutated USP8 was generated by mutagenic PCR. The corresponding protein encodes a cysteine to alanine substitution at residue 786. The sequences were ascertained by sequencing of the entire open reading frame. Bacmids encoding USP8 were generated following DH10bac transposition. The corresponding bacmids were transfected into insect cells (Sf9). Viruses were recovered from culture supernatant and amplified twice. Insect cells (Sf9 or High Five; Invitrogen) were infected for 72 hours. Total cell lysates were harvested and lyzed in lysis buffer (Tris HCl 50 mM pH7.6; 0.75% NP40; 500 mM NaCl; 10% glycerol; 1 mM DTT; 10 mM imidazole; Protease Inhibitor Cocktail; AEBSF 20 µg·ml$^{-1}$; Aprotinin 10 µg·ml$^{-1}$). Proteins were affinity purified on metal affinity resins (Talon Metal affinity resin; BD Biosciences). Bound materials were extensively washed in wash buffer (50 mM Sodium Phosphate pH 7.0; 300 mM NaCl; 10 mM imidazole; 0.5% Triton X-100; 10% glycerol) and eluted from the resin in 250 mM imidazole-containing wash buffer. Proteins were dialyzed in dialysis buffer (Tris HCl pH 7.6 20 mM; NaCl 200 mM; DTT 1 mM; EDTA 1 mM; 10% Glycerol). Proteins purifications were analyzed on 4-12% NuPAGE (Invitrogen).

USP8 Activity Assay

USP8 was diluted in USP buffer (50 mM Tris HCl; 0.5 mM EDTA; 5 mM DTT; 0.01% Triton X-100; Bovine Serum Albumin 0.05 mg·ml$^{-1}$ pH8.8). Compounds stocks (100 mM) were stored at –20° C. in DMSO. Compounds were tested at different concentrations: from 200 µM to 91 nM.

Reactions were performed as duplicates in Black 384 well plates (small volume microplates; Greiner; 10 µl final reaction volume). The substrate concentration for USP8 was 300 nM Ub-AMC (Boston Biochem). The concentration of the enzyme (USP8) in specificity assays was 1.36 nM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/– compounds) diluted in assay buffer. Reactions were incubated for 60 minutes at 37° C. Reactions were stopped by adding acetic acid (100 mM final). Readings were performed on a Pherastar Fluorescent Reader (BMG). λ Emission 380 nm: λ Excitation=460 nm. Data (mean values +/– standard deviation) were analyzed as % of control (no compound) and plotted as percentage versus the Log of the compound concentration using GraphPad (Prism). Data were fitted to a sigmoidal model (variable slope).

UCH-L1 Activity Assay

UCH-L1 was diluted in USP buffer (50 mM Tris HCl; 0.5 mM EDTA; 5 mM DTT; 0.01% Triton X-100; Bovine Serum Albumin 0.05 mg·ml$^{-1}$ pH7.6). Compounds stocks (100 mM) were stored at –20° C. in DMSO. Compounds were tested at different concentrations: from 200 µM to 91 nM.

Reactions were performed as duplicates in Black 384 well plates (small volume microplates; Greiner; 10 µl final reaction volume). The substrate concentration for UCH-L1 was 300 nM Ub-AMC (Boston Biochem). The concentration of the enzyme (UCH-L1) in specificity assays was 2.5 nM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/– compounds) diluted in assay buffer. Reactions were incubated for 60 minutes at 37° C. Reactions were stopped by adding acetic acid (100 mM final). Readings were performed on a Pherastar Fluorescent Reader (BMG). λ Emission 380 nm; λ Excitation=460 nm. Data (mean values +/– standard deviation) were analyzed as % of control (no compound) and plotted as percentage versus the Log of the compound concentration using GraphPad (Prism). Data were fitted to a sigmoidal model (variable slope).

UCH-L3 Activity Assay

UCH-L3 was diluted in USP buffer (50 mM Tris HCl; 0.5 mM EDTA; 5 mM DTT; 0.01% Triton X-100; Bovine Serum Albumin 0.05 mg·ml$^{-1}$ pH7.6). Compounds stocks (100 mM) were stored at –20° C. in DMSO. Compounds were tested at different concentrations: from 200 µM to 91 nM.

Reactions were performed as duplicates in Black 384 well plates (small volume microplates; Greiner; 10 µl final reaction volume). The substrate concentration for UCH-L3 was 300 nM Ub-AMC (Boston Biochem). The concentration of the enzyme (UCH-L3) in specificity assays was 13 pM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/– compounds) diluted in assay buffer. Reactions were incubated for 60 minutes at 37° C. Reactions were stopped by adding acetic acid (100 mM final). Readings were performed on a Pherastar Fluorescent Reader (BMG). λ Emission 380 nm; λ Excitation=460 nm. Data (mean values +/– standard deviation) were analyzed as % of control (no compound) and plotted as percentage versus the Log of the compound concentration using GraphPad (Prism). Data were fitted to a sigmoidal model (variable slope).

Caspase 3 Activity Assay

Caspase 3 was diluted in Caspase 3 buffer (100 mM Hepes pH 7.5; 10% sucrose; 0.1% CHAPS). Compounds stocks (100 mM) were stored at –20° C. in DMSO. Compounds were tested at different concentrations: from 200 µM to 91 nM.

Reactions were performed as duplicates in Black 384 well plates (small volume microplates; Greiner; 10 µl final reaction volume). The substrate concentration for caspase 3 specificity assay was 250 nM (Ac-DEVD-AMC; Promega). The concentration of the enzyme (Caspase 3) in specificity assays was 1.6 nM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/– compounds) diluted in assay buffer. Reactions were incubated for 60 minutes at 37° C. Reactions were stopped by adding acetic acid (100 mM final). Readings were performed on a Pherastar Fluorescent Reader (BMG). λ Emission 380 nm; λ Excitation=460 nm. Data (mean values+/– standard deviation) were analyzed as % of control (no compound) and plotted as percentage versus the Log of the compound concentration using GraphPad (Prism). Data were fitted to a sigmoidal model (variable slope).

Cell Viability and Proliferation Methods

HCT116 Cell Viability and Proliferation Assay

HCT116 colon cancer cells were obtained from ATCC (American Type Culture Collection), and maintained in Mc Coy's 5A medium containing 10% FBS, 3 mM glutamine and 1% penicillin/streptomycin. Cells were incubated at 37° C. in a humidified atmosphere containing 5% $CO_2$.

Cell viability was assayed using the MTS technique in 96-well culture plates (CellTiter 96® Aqueous Non-Radioactive Cell Proliferation Assay, Promega) according to the manufacturer's instructions. MTS (3-(4,5-dimethyl-thiazol-2-yl)-5-(3-carboxy-methoxyphenyl)-2-(4-sulfophenyl)-2H-tetra-zolium) is a MTT-derived tetrazolium that is reduced in metabolically active cells into a soluble, cell-permeant formazan. The amount of formazan, detected by its absorbance at 492 nm is proportional to the number of living, metabolically active cells.

$10^3$ HCT116 cells were seeded per well. 24 hours later, the medium was changed and the cells treated in triplicate with the concentrations of each compound from 100 μM to 50 nM. The compounds were diluted in 100% DMSO, whose final concentration on cells was kept at 0.5%.

Cells were incubated with the compounds for 72 hours, and their viability then assayed by the addition of MTS for 2 hours. Absorbance at 492 nm was measured directly from the 96-well culture plates. GI50 (Growth Inhibition 50) concentrations for each compound were calculated using a sigmoidal variable slope fit (Prism 4.0, Graphpad Softwares). Values represent mean of three independent experiments.

Methods for Evaluation of Compound Selectivity from a Panel of Deubiquitinating Enzymes Active in Cell Lysates The C-terminally modified vinyl sulfone derivative of ubiquitin, UbVS, was clearly helpful for a direct visualization of active DUBs in cells. This tool, which binds covalently to the cysteine active site of deubiquitinating enzymes, was successfully applied to discover and characterize novel ubiquitin/ubiquitin-like proteases and to profile active deubiquitinating enzymes in normal, virus-infected, and malignant cells (Borodovsky et al., *Chem Biol* 2002, 9, 1149-1159, Hemelaar et al., *Mol Cell Biol* 2004, 24, 84-95, Ovaa et al., *Proc Natl Acad Sci USA* 2004 101, 2253-2258).

The HA-Ub-VS probe (Hemagglutin tag-Ubiquitin-Vinyl Sulfone) was used in this study to directly visualize the activity of all deubiquitinating enzymes from cell lysates. This tool was used to evaluate the activity/specificity of our small molecule compounds on USP7 relative to all deubiquitinating enzymes active in physiological conditions.

Inducible USP7 shRNA HCT116 cells (previously treated with or without Doxycycline (2 μg/ml) for 4 days) as well as HEK293 cells were harvested and lysed on ice with a non denaturating buffer containing Tris pH7.4, 50 mM; NaCl, 150 mM; $MgCl_2$, 5 mM; EDTA, 0.5 mM; DTT, 2 mM; ATP, 2 mM; NP40, 0.5% and glycerol, 10%. Samples were incubated at 4° C. for 1 hour and clarified. Proteins were then quantified by Bradford method (Bio-Rad Protein Assay). 25 μg of proteins from native cell lysates were treated with compounds of examples 14 and 5 (from 100 μM to 3 μM) or with NEM (N-Ethylmaleimide, a thiol-reactive compound, 5 mM) for 2 hours at room temperature. The ubiquitin labeling reaction was initiated by the addition of HA-Ub-VS (8 μg/ml) in labeling buffer (Tris pH7.6, 50 mM; $MgCl_2$, 5 mM; EDTA, 0.5 mM; DTT, 2 mM; ATP, 2 mM; sucrose, 250 mM) and incubated at room temperature for 30 min. Samples were next heated at 100° C. for 10 minutes and briefly sonicated. They were resolved by SDS-polyacrylamide gel electrophoresis (SDS-PAGE), transferred to a nitrocellulose membrane and probed with antibodies against USP7 (Bethyl Lab, A300-034A), HA (BabCO, MMS-101P), and actin (Sigma, A2066). Horseradish peroxidase (HRP)-conjugated anti-mouse (Jackson Laboratories, 115-035-003) or HRP-conjugated anti-rabbit (Cell Signaling, 7074) antibodies were used as secondary antibodies. Signals were detected by enhanced chemiluminescence (ECL; Amersham) according to the reagent manufacturer's instructions.

Results

1. Selective Inhibition of USP7 Deubiquitinating Activity
The results are summarized on the following table (μM):

| Example | MW | USP7 | USP8 | USP5 | Uch-L1 | Uch-L3 | Caspase 3 |
|---|---|---|---|---|---|---|---|
| 1 | 462.04 | 9.1 | >200 | >200 | >200 | >200 | >200 |
| 2 | 371.91 | 11.5 | >200 | >200 | >200 | >200 | >200 |
| 3 | 387.96 | 12.4 | >200 | >200 | >200 | >200 | >200 |
| 4 | 387.96 | 23.5 | >200 | >200 | >200 | >200 | >200 |
| 5 | 436.00 | 22.6 | >200 | >200 | >200 | >200 | >200 |
| 6 | 401.98 | 23.8 | >200 | >200 | >200 | >200 | >200 |
| 7 | 359.90 | 24.9 | >200 | >200 | >200 | >200 | >200 |
| 8 | 371.91 | 25.6 | >200 | >200 | >200 | >200 | >200 |
| 9 | 414.00 | 28.7 | >200 | >200 | >200 | >200 | >200 |
| 14 | 421.97 | 28.1 | >200 | >200 | >200 | >200 | >200 |
| 10 | 373.93 | 29.2 | >200 | >200 | >200 | >200 | >200 |
| 11 | 331.85 | 29.8 | >200 | >200 | >200 | >200 | >200 |
| 12 | 342.87 | 37.9 | >200 | >200 | >200 | >200 | >200 |
| 13 | 429.01 | 37.9 | >200 | >200 | >200 | >200 | >200 |
| 15 | 400.96 | 43.0 | >200 | >200 | >200 | >200 | >200 |
| 16 | 411.98 | 46.0 | >200 | >200 | >200 | >200 | >200 |
| 17 | 371.91 | 13.7 | >200 | >200 | >200 | >200 | >200 |
| 18 | 433.98 | 18.3 | >200 | >200 | >200 | >200 | >200 |
| 19 | 419.96 | 8.2 | >200 | >200 | >200 | >200 | >200 |
| 20 | 399.97 | 45.5 | >200 | >200 | >200 | >200 | >200 |
| 21 | 433.98 | 16.3 | >200 | >200 | >200 | >200 | >200 |
| 22 | 478.04 | 27.4 | >200 | >200 | >200 | >200 | >200 |
| 23 | 491.08 | 33.1 | >200 | >200 | >200 | >200 | >200 |
| 24 | 357.88 | 45.2 | ~200 | >200 | >200 | >200 | >200 |
| 25 | 478.04 | 59.5 | >200 | >200 | >200 | >200 | >200 |
| 26 | 432.82 | 30.5 | >200 | >200 | >200 | >200 | >200 |

2. Inhibition of Cell Viability/Proliferation
The results are summarized on the following table (μM):

| Example | MW | MLogP | Cell viability (MTS): HCT116 $GI_{50}$ Day3 (μM) |
|---|---|---|---|
| 1 | 462.04 | 4.5 | 2.0 |
| 2 | 371.91 | 3.3 | 5.0 |
| 3 | 387.96 | 3.5 | 3.5 |
| 4 | 387.96 | 3.5 | 4.0 |
| 5 | 436.00 | 4.1 | 4.0 |
| 6 | 401.98 | 3.7 | 3.9 |
| 7 | 359.9 | 3.0 | 4.3 |
| 8 | 371.91 | 3.3 | 5.9 |
| 9 | 414.00 | 3.9 | 3.6 |
| 10 | 373.93 | 3.3 | 5.0 |
| 11 | 331.85 | 2.6 | 7.8 |
| 12 | 342.87 | 3.9 | 20 |
| 13 | 429.01 | 3.1 | 5.9 |
| 14 | 421.97 | 3.9 | 4.1 |
| 15 | 400.96 | 2.7 | 7.4 |
| 16 | 411.98 | 3.9 | 13.5 |
| 17 | 371.91 | 3.3 | 6.9 |
| 18 | 433.98 | 4.1 | 4.3 |
| 19 | 419.96 | 4.1 | 4.1 |
| 20 | 399.97 | 3.7 | 8.4 |
| 21 | 433.98 | 4.1 | 3.5 |
| 22 | 478.04 | 4 | 3.3 |
| 23 | 491.08 | 4.1 | 1.8 |
| 24 | 357.88 | 3 | 8.3 |
| 25 | 478.04 | 3.7 | 5.6 |
| 26 | 432.82 | 3.5 | 5.6 |
| 27 | 385.94 | 3.5 | 10.0 |
| 28 | 371.91 | 3.3 | 8.8 |
| 29 | 441.02 | 3.3 | 7.3 |
| 30 | 426.99 | 3.1 | 12.5 |
| 31 | 328.84 | 3.6 | 11.4 |

-continued

| Example | MW | MLogP | Cell viability (MTS): HCT116 GI$_{50}$ Day3 (μM) |
|---|---|---|---|
| 32 | 448.01 | 4.3 | 3.1 |
| 33 | 476.06 | 4.7 | 2.0 |
| 34 | 462.04 | 4.5 | 2.8 |
| 35 | 401.98 | 3.7 | 8.2 |
| 36 | 371.91 | 3.3 | 9.1 |
| 37 | 371.91 | 3.3 | 8.7 |
| 38 | 373.93 | 3.3 | 11 |
| 39 | 433.98 | 4.1 | 7.6 |

3. Selective Inhibition of USP7 Deubiquitinating Activity Over a Panel of Active DUBs in Physiological Conditions:

As summarized in FIG. 1A, the C-terminally modified vinyl sulfone derivative of ubiquitin (HA-Ub-VS), binds covalently to the cysteine active site of deubiquitinating enzymes. This labeling followed by immunoblot with the anti-HA antibody allowed the identification of all active deubiquitinating enzymes from HCT116 cell lysates (FIG. 1B). In addition, active USP7 was identified in this assay as indicated by the mobility shift observed following immunoblot with anti-USP7 antibody. This labeling, specific to the active form of DUBs, is inhibited by a thiol-reactive compound (NEM) in a non-specific manner (FIG. 1B).

Figure 2A:
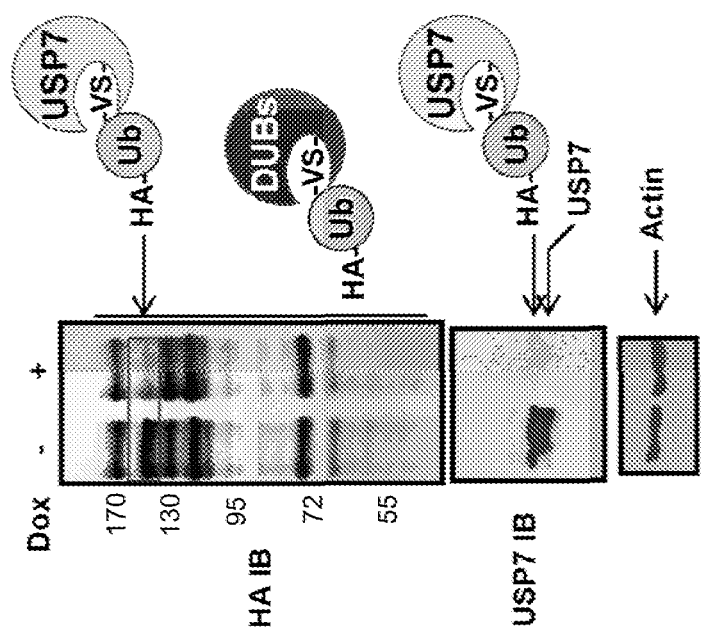
FIG. 2A shows the localized signal corresponding to active USP7 in the panel of active DUBs following HA-Ub-VS labeling, by treating the inducible shRNA USP7 HCT116 cell line with Doxycycline (Dox) thus enabling the expression of USP7 shRNA. Interestingly, only one band was decreased following USP7 silencing thus clearly indicating that this band corresponds to HA-Ub-VS-USP7.

To localize the signal corresponding to active USP7 in the panel of active DUBs following HA-Ub-VS labeling, the inducible shRNA USP7 HCT116 cell line was treated with Doxycycline (Dox) thus enabling the expression of USP7 shRNA. Interestingly, only one band was decreased following USP7 silencing thus clearly indicating that this band corresponds to HA-Ub-VS-USP7 (FIG. 2A). A quantification showing this specific decrease is presented in FIG. 2B (quantification performed using the image analysis software, GeneTools, Syngene). USP7 silencing induced by Doxycycline treatment was confirmed with anti-USP7 antibody.

Figure 3B:
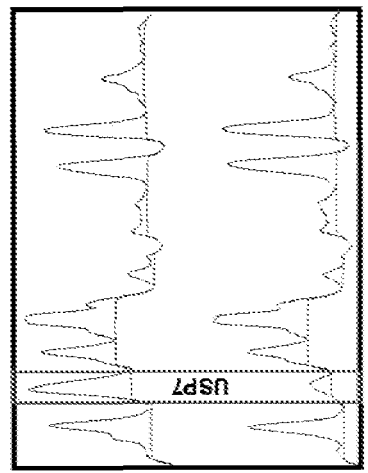
FIG. 3B shows a quantification of the specific decrease of FIG. 3A (quantification performed using the image analysis software, GeneTools, Syngene). This effect on USP7 activity was confirmed with anti-USP7 antibody as indicated by the mobility shift observed between the treated and non-treated samples.
Figure 3A:
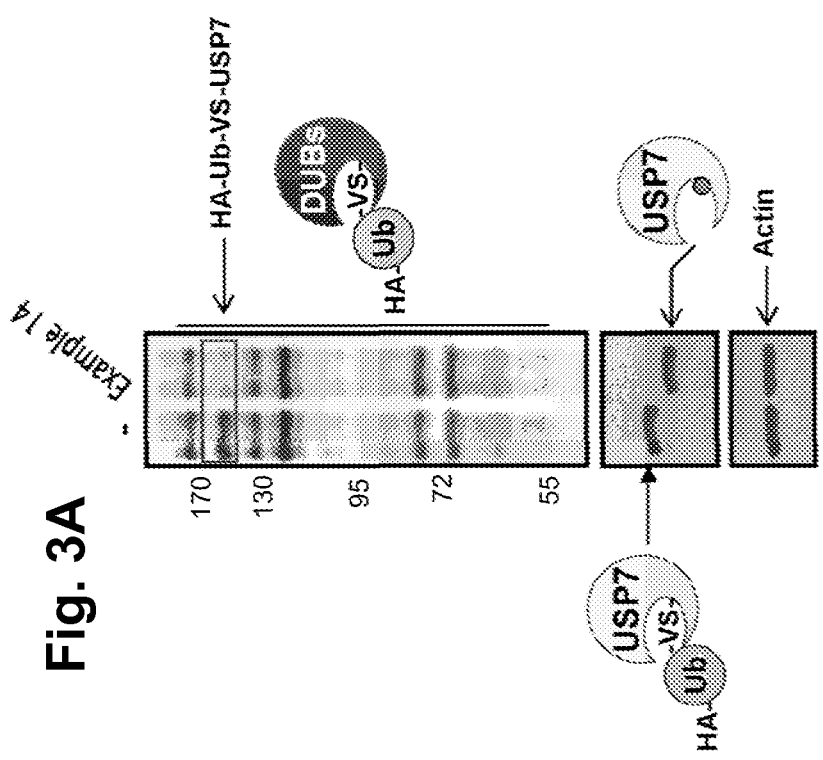
FIG. 3A shows a study with small molecule compound first performed with a fixed dose of the compound of example 14 (50 µM) on HCT116 cell lysates. Interestingly, only one band was decreased following treatment at the size corresponding to HA-Ub-VS-USP7.

A study with small molecule compound was first performed with a fixed dose of the compound of example 14 (50 μM) on HCT116 cell lysates. Interestingly, only one band was decreased following treatment at the size corresponding to HA-Ub-VS-USP7 (FIG. 3A). A quantification showing this specific decrease is presented in FIG. 3B (quantification performed using the image analysis software, GeneTools, Syngene). This effect on USP7 activity was confirmed with anti-USP7 antibody as indicated by the mobility shift observed between the treated and non-treated samples.

HCT116 cells were next treated either with different doses of compounds of examples 14 and 5 or with Doxycycline to induce USP7 silencing. Localization of the HA-Ub-VS-USP7 protein was facilitated by the specific silencing of USP7 as indicated in the presence of doxycycline (FIG. 4A, +Dox). Once this band identified, cell lysates were treated with different doses of compounds of examples 14 and 5 and a specific and dose-dependent decrease of the HA-Ub-VS-USP7 protein level was clearly observed (FIGS. 4A and B). This effect on USP7 activity was confirmed with anti-USP7 antibody as indicated by the mobility shift observed between the treated and non-treated samples. Interestingly, these findings were also confirmed in cell lysates prepared from HEK293 cells (FIGS. 5A and B). These results thus demonstrate that different compounds from this new chemical series (compounds of examples 14 and 5) inhibit specifically and dose-dependently USP7 deubiquitinating activity over a panel of active DUBs in physiological conditions.

4. Use of Ub52 as USP7 and USP8 Substrate for Evaluation of USP Modulators

For compounds 26 to 38, the in-vitro assays on USP7 and USP8 were carried out according to the following procedure Preparation of Ubiquitin-Ribosomal Protein Fusions A cDNA encoding the fusion protein between ubiquitin and the ribosomal protein L40 (ub52 or uba52 or ubiquitin-L40) was amplified from human RNA using a proprietary human placenta library. The cDNA was subcloned into a bacterial expression vector (pGEX-2T, GE Healthcare), including an additional flag tag at the carboxyl end of the encoded protein. The following primers were used for subcloning in frame with the GST tag the ubiquitin-L40 into pGEX-2T: 5'-cgtggatccatgcagatctttgtgaagaccctc-3' (SEQ ID NO:10) and 5'-gcgaattctttatcgtcatcgtctttg-tagtctttgaccttcttcttgggacg-3' (SEQ ID NO:11) into BamHI & EcoRI restriction sites.

For production and purification of recombinant proteins, the plasmid pGEX-2T-Ub52-flag was transformed into E. coli BL21 (Stratagene), grown in LB medium supplemented with 100 mg/ml ampicilin (LB ampi) at 37° C. overnight and then diluted 1/100 in LB ampi. The cells were incubated at 37° C. until an A600=0.6-0.8 was reached. After induction with 0.1 mM isopropyl-β-D-thiogalactopyranoside (IPTG), the culture was incubated at 30° C. for 180 min.

Cells were harvested by centrifugation for 15 min at 7000×g at 4° C. Bacterial pellets were lysed in NETN (Tris HCl pH 8.0; EDTA 1 mM; NP40 0.5%; protease inhibitor cocktail, PMSF 1 mM) and briefly sonicated. Insoluble material was removed by centrifugation 30 min at 14000×g. GST-Ub52-flag proteins were purified according to Everett R D et al., EMBO J. (1997) 16, 1519-1530. Briefly, soluble fraction was incubated on Glutathione beads pre-equilibrated in NETN buffer+0.5% Milk for 120 min at 4° C. Flow Through was recovered. Beads were extensively washed: the last wash was performed in Tris HCl pH 7.6 20 mM; NaCl 100 mM; MgCl$_2$ 12 mM. Elutions were performed using 20 mM Reduced Glutathione in 50 mM Tris HCl pH 8.0, NaCl 120 mM. All fractions were resolved on a 4-12% NuPAGE following 0.1 M DTT treatment and denaturation and stained with Coomassie Brilliant Blue. Elutions were dialysed over night at 4° C. in Tris HCl pH 7.6 20 mM; NaCl 50 mM; DTT 0.5 mM.

Assaying the Fusion Protein (GST-Ub52-Flag) Using Homogenous Time-Resolved Fluorescence (HTRF®) Measurement Method The present examples 26 to 38 makes it possible to validate the use of GST-Ub52-Flag in an assay based on the time-resolved measurement of fluorescence emitted by radioactive transfer in homogenous medium.

The reagents used were as follows:

Anti-flag antibody-europium cryptate conjugate referred to as anti-Flag-K (CIS bio international), solution at 0.2 μM in 0.8 M KF, 0.1% Bovine Serum Albumin, Tris HCl 25 mM pH 7.6.

Anti-GST antibody-XL665 conjugate (CIS bio international), solution at 2.6 μM in 0.8 M KF, 0.1% Bovine Serum Albumin, Tris HCl 25 mM pH 7.6.

GST-Ub52-Flag solution at 14.75 μM & MBP_Ub52 at 37.7 μM prepared from the stock solution described above in 50 mM Tris HCl pH 7.6, EDTA 0.5 mM, Bovine Serum Albumin 0.05%, DTT 5 mM.

The assay is carried out on multiwell assay plates. The plates are analyzed on a PHERAstar fluorimeter (BMG) after an overnight incubation at 4° C. (excitation 337 nm, emission 620 and 665 nm).

Assaying the Activity of Enzymes of the Deubiquitinating Type with Ubiquitin-Ribosomal Protein Fusion The reagents used were as follows:
Solution of USP7 at 200 pM and USP8 at 400 pM in 50 mM Tris HCl pH 7.6, Bovine Serum Albumin 0.05%, DTT 5 mM.
Anti-Flag-K (CIS bio international), solution at 0.2 µM in 0.8 M KF, 0.1 Bovine Serum Albumin, Tris HCl 25 mM pH 7.6.
Anti-GST antibody-XL665 conjugate (CIS bio international), solution at 2.6 µM in 0.8 M KF, 0.1% Bovine Serum Albumin, Tris HCl 25 mM pH 7.6.
GST-Ub52-flag solution at 14.75 µM & MBP_Ub52 at 37.7 µM are prepared by dilutions from the stock solution described above in 50 mM Tris HCl pH 7.6, EDTA 0.5 mM, Bovine Serum Albumin 0.05%, DTT 5 mM.

The enzyme reaction is carried out by mixing GST-Ub52-flag solution with 5 µl of USP7 solution (200 pM final) or 5 µl of USP8 (400 pM final). This mixture is incubated for one hour at room temperature on a multiwell assay plate. A 10 µl mixture of 5 µl of anti-Flag-K solution (0.2 µM) plus 5 µl of anti-GST-XL665 antibody (2.6 µM) is added to each well of the multiwell assay plate. The plate is read after an overnight incubation at 4° C. on a PHERAstar fluorimeter (BMG).

The decrease in the signal correlates with the increase in enzyme activity i.e. the cleavage of GST-Ub52-Flag substrate. The format used is therefore entirely suitable for a method of assaying an enzyme of the deubiquitinating type such as ubiquitin specific protease, but also for determining a modulator of this enzyme activity.

Determination of a Modulator of Enzyme Activity of the Deubiquitinating Type

The same procedures as mentioned above for assaying the activity of enzymes of the deubiquitinating type are carried out but the various reaction mixtures are incubated with identical enzyme concentration, in the presence or absence of a test compounds 26 to 38. Data (mean values+/− standard deviation) were analyzed as % of control (no compound) and plotted as percentage versus the Log of the compound concentration using GraphPad (Prism). Data were fitted to a sigmoidal model (variable slope) and IC$_{50}$ (µM) was determined and presented in the following table.

| Example | MW | USP7 | USP8 |
| --- | --- | --- | --- |
| 27 | 385.94 | 15.4 | >200 |
| 28 | 371.91 | 11.9 | >200 |
| 29 | 441.02 | 8.5 | >200 |
| 30 | 426.99 | 23 | >200 |
| 31 | 328.84 | 24.5 | >200 |
| 32 | 448.01 | 17.6 | >200 |
| 33 | 476.06 | 16.4 | >200 |
| 34 | 462.04 | 24.5 | >200 |
| 35 | 401.98 | 36.9 | >200 |
| 36 | 371.91 | 44.4 | >200 |
| 37 | 371.91 | 25.9 | >200 |
| 38 | 373.93 | 49.2 | >200 |
| 39 | 433.98 | 38.5 | >200 |

The invention claimed is:
1. A method for inhibiting a USP7 comprising administering to a patient in need thereof a compound of formula (I)

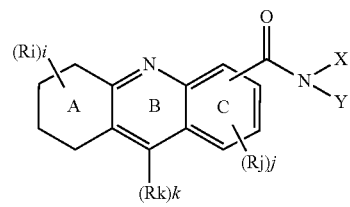

wherein:
 i is 0
 j is 0
 k is 1;
 each Ri located on any available position of the A ring is identical or different and chosen from halogen, alkyl, aryl, -alkylaryl, OR, NRR', CN, CF$_3$, COR, COOR, CONRR';
 each Rj located on any available position of the C ring is identical or different and chosen from halogen, alkyl, aryl, -alkylaryl, OR, NRR', CN, COR, COOR, CONRR';
 Rk is chosen from halogen;
 X is H;
 Y is chosen from:
  (CHT')$_p$NRaRb where
   Ra and Rb, identical or different, are independently chosen from alkyl, aryl or aralkyl;
 or Ra and Rb together form with the N atom to which they are attached a N comprising 5 to 7-membered heterocycle which may comprise one or two more heteroatoms chosen from N, O or S, said heterocycle being optionally substituted by one or more of alkyl;
 p is an integer chosen from 0 to 6;
 each T', identical or different is independently chosen from H or alkyl;

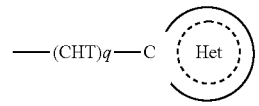

wherein:

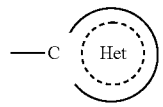

is a saturated or partially unsaturated heterocycle or heteroaryl, mono or bicyclic, comprising 1, 2 or 3 heteroatom(s) chosen from N, O or S, optionally substituted by one or more of alkyl; -alkylaryl; C(=O)OR wherein said aryl is optionally substituted by alkyl;
 q is an integer chosen from 0 to 6;
 each T, identical or different is independently chosen from H or alkyl;
(CHT)$_r$-aryl wherein:
 said mono or bicyclic aryl is optionally substituted by one or more of alkyl;
 r is an integer chosen from 0 to 6;
 each T, identical or different is independently chosen from H or alkyl;

or X and Y together form with the N atom to which they are attached an heterocycle comprising said N atom and optionally one or two more heteroatoms, said heterocyle being optionally insaturated and/or being optionally substituted by one or more of alkyl; heterocycle; or -alkylaryl or being optionally fused with an aryl;

where R and R', identical or different are independently chosen from H, alkyl, aryl, -alkylaryl, or a tautomer thereof, and/or a pharmaceutically acceptable salt thereof, and wherein the compound of formula (I) is not a compound of formula (I) wherein Rk is Cl, i=j=0, and:
  X is H and Y is a phenyl substituted by CN or —C(=O)CH$_3$; or
  X and Y together form a piperazinyl ring substituted by a methoxyphenyl or fluorophenyl; or
  X and Y together form a piperidyl ring substituted by a piperidyl; or
  one of X is H and Y is a piperidyl substituted with COOEt.

2. The method according to claim 1 wherein the compound of formula (I) or a tautomer thereof, and/or a pharmaceutically acceptable salt thereof, is combined with one or more active agents chosen from anti-cancer agents, neurological agents, thrombolytic agents, antioxidant agents, anti-infective, anti-hypertensive agents, diuretic agents, thrombolytic agents, immunosuppressive agents, cardiovascular agents, immunomodulatory agents, anti-inflammatory agents, antiviral agents, anti-bacterial agents.

3. A method of inhibiting USP7 comprising administering to a patient in need thereof a compound chosen among
  9-Chloro-5,6,7,8-tetrahydro-acridine-3-carboxylic acid [1-(3-methyl-benzyl)-piperidin-4-ylmethyl]-amide,
  9-Chloro-5,6,7,8-tetrahydro-acridine-3-carboxylic acid (1-ethyl-pyrrolidin-2-ylmethyl)-amide,
  9-Chloro-5,6,7,8-tetrahydro-acridine-3-carboxylic acid (2-dipropylamino-ethyl)-amide,
  9-Chloro-5,6,7,8-tetrahydro-acridine-3-carboxylic acid [2-(butyl-ethyl-amino)-ethyl]-amide,
  9-Chloro-5,6,7,8-tetrahydro-acridine-3-carboxylic acid [3-(benzyl-ethyl-amino)-propyl]-amide,
  9-Chloro-5,6,7,8-tetrahydro-acridine-3-carboxylic acid (3-dipropylamino-propyl)-amide,
  9-Chloro-5,6,7,8-tetrahydro-acridine-3-carboxylic acid (2-diethylamino-ethyl)-amide,
  9-Chloro-5,6,7,8-tetrahydro-acridine-3-carboxylic acid (3-pyrrolidin-1-yl-propyl)-amide,
  9-Chloro-5,6,7,8-tetrahydro-acridine-3-carboxylic acid [3-(2,6-dimethyl-piperidin-1-yl)-propyl]-amide,
  9-Chloro-5,6,7,8-tetrahydro-acridine-3-carboxylic acid (3-diethylamino-propyl)-amide,
  9-Chloro-5,6,7,8-tetrahydro-acridine-3-carboxylic acid (2-dimethylamino-ethyl)-amide,
  Azepan-1-yl-(9-chloro-5,6,7,8-tetrahydro-acridin-3-yl)-methanone,
  9-Chloro-5,6,7,8-tetrahydro-acridine-3-carboxylic acid [3-(4-propyl-piperazin-1-yl)-propyl]-amide,
  9-Chloro-5,6,7,8-tetrahydro-acridine-3-carboxylic acid [3-(benzyl-methyl-amino)-propyl]-amide,
  9-Chloro-5,6,7,8-tetrahydro-acridine-3-carboxylic acid [3-(4-methyl-piperazin-1-yl)-propyl]-amide,
  [1,4']Bipiperidinyl-1'-yl-(9-chloro-5,6,7,8-tetrahydro-acridin-3-yl)-methanone,
  or a tautomer thereof, and/or a pharmaceutically acceptable salt thereof.

4. The method according to claim 1, wherein the administration of the compound of formula (I) to inhibit USP7 is for the specific treatment of colon cancer.

* * * * *